United States Patent
Kadiyala et al.

(10) Patent No.: US 7,659,240 B2
(45) Date of Patent: Feb. 9, 2010

(54) MUCIN IMMOBILIZED CHROMATOGRAPHY

(75) Inventors: Irina Kadiyala, South Easton, MA (US); Riccardo Panicucci, Billerica, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 512 days.

(21) Appl. No.: 10/345,453

(22) Filed: Jan. 14, 2003

(65) Prior Publication Data
US 2003/0171558 A1 Sep. 11, 2003

Related U.S. Application Data

(60) Provisional application No. 60/348,184, filed on Jan. 14, 2002.

(51) Int. Cl.
C07K 14/00 (2006.01)
(52) U.S. Cl. .......................................... 514/2; 530/350
(58) Field of Classification Search ................. 530/350; 514/2
See application file for complete search history.

(56) References Cited

U.S. PATENT DOCUMENTS

| | | | |
|---|---|---|---|
| 4,247,452 A | 1/1981 | Irons et al. | 260/112 R |
| 4,722,917 A | 2/1988 | Seno et al. | 502/7 |
| 4,818,682 A | 4/1989 | Linnane | 435/7 |
| 4,851,357 A | 7/1989 | Yamashina | 436/528 |
| 4,921,644 A * | 5/1990 | Lau et al. | 264/4.1 |
| 4,927,879 A | 5/1990 | Pidgeon | 525/54.1 |
| 4,931,498 A * | 6/1990 | Pidgeon | 525/54.1 |
| 5,008,184 A | 4/1991 | Linnane | 435/7.23 |
| 5,075,218 A | 12/1991 | Jette et al. | 435/7.23 |
| 5,731,006 A | 3/1998 | Akiyama et al. | 424/502 |
| 5,827,666 A | 10/1998 | Finn et al. | 435/7.1 |
| 5,846,955 A | 12/1998 | Pidgeon et al. | 514/77 |
| 5,989,552 A | 11/1999 | McKenzie et al. | 424/185 |
| 6,177,256 B1 | 1/2001 | McKenzie et al. | 435/7.23 |
| 6,235,709 B1 * | 5/2001 | Kodama et al. | 514/2 |

FOREIGN PATENT DOCUMENTS

| WO | WO 89/08130 | | 9/1989 |
|---|---|---|---|
| WO | WO-0246760 | * | 6/2002 |

OTHER PUBLICATIONS

Iida et al. 1999; Interaction of human macrophage C-type lectin with O-linked N-acetylgalactosamine residues on mucin glycopeptides. J. Biol. Chem. 274(16): 10697-10705.*
Jiang et al. 1998; Sequence of a second gene encoding bovine mucin: Implication for mucin heterogeneity and cloning. Biochem. Biophys. Res. Commun. 251: 550-556.*
Song et al. 1999; Lectinochemical characterization of a GalNAc and multi-Gal☐1->4GlcNAc reactive lectin from *Wisteria sinensis* seeds. Eur. J. Biochem 266: 778-788.*

Swarnakar et al. 1991; N-glycolyneuraminic acid specific lectin from *Pila globosa* snail. Biochem. Biophys. Res. Commun. 178(1): 85-94.*
Alebić-Kolbah, T., et al., "Enzyme-based high-performance liquid chromatography stationary phases as metabolic reactors: Immobilization of non-solubilized rat liver microsomes on an Immobilized artificial membrane high-performance liquid chromatography support," J. Chromatography, 646:289-295 (1993).
Artursson, P., et al. "Correlation between oral drug absorption in humans and apparent drug permeability coefficients in human intestinal epithelial (CACO-2) cells," Biochemical and Biophysical Research Communications, 175(3): 880-885 (1991).
Bangham, A.D., et al., "Preparation and use of liposomes as models of biological membranes," Methods in Mebrane Biology, 1-68 (1974).
Barthe, L., et al., "An improved everted gut sac as a simple and accurate technique to measure paracellular transport across the small intestine," Eur. J. Drug Metab. Pharmocokinet., 23:313-323 , (1998).
Bhavanandan, V.P., "Cancer-associated mucins and mucin-type glycoproteins," Glycobiology, 1(5):493-503 (1991).
Braybrooks, M.P., et al., "The effect of mucin on the bioavailability of tetracyline from the gastrointestinal tract; in vivo, in vitro correlations," J. Pharm. Pharmac., 27:508-515 (1975).
Caldwell, G.W., et al., "Evaluation of the immobilized artificial membrane phosphatidylcholine: Drug discovery column for high-performance liquid chromatographic screening of drug-membrane interactions," Journal of Chromatography A, 800:161-169 (1998).
Caraway, K.L., et al., "Cell surface mucin-type glycoproteins and mucin-like domains," Glycobiology, 1(2):131-138 (1991).
Chui, W-K., et al., "Enzyme-based high-performance liquid chromatography supports as probes of enzyme activity and inhibition: The mobilization of trypsin and a-chymotrypsin on an immobilized artificial membrane high-performance liquid chromatography support," Analytical Biochemistry, 201:237-245 (1992).
Ciborowski, P., et al., "Expression of MUC1 in insect cells using recombinant baculovirus," *Glycoprotein Methods and Protocols: The Mucins*, A.P. Corfield, Humana,Press, Totowa, New Jersey, 125:471-487 (2000).
Corfield, A.P., et al., "Mucins in the gastrointestinal tract in health and disease," Front. Biosci., 6, d1321-1357 (2001).

(Continued)

Primary Examiner—Karen Cochrane Carlson
(74) Attorney, Agent, or Firm—Ropes & Gray LLP; James F. Haley, Jr.; Jane H. Bu

(57) ABSTRACT

An in vitro high-throughput screening method that models the absorption of drugs across the epithelial mucosa is provided. The invention discloses an in vitro mucin immobilized chromatography model to estimate drug permeability coefficients. The invention describes compositions for mucin immobilized chromatography media and methods to prepare this media. The invention also discloses a method to estimate in vitro drug permeability coefficients using mucin immobilized chromatography media. The invention also discloses methods to determine absorption processes in the digestive system and discloses methods of use for mucin chromatography media in column, batch, assay, diagnostic, or high-throughput screening analyses.

18 Claims, 9 Drawing Sheets

OTHER PUBLICATIONS

Dolby, N., et al. "Design and expression of a synthetic mucin gene fragment in *Escherichia coli*," *Protein Expression and Purification*, 15:146-154 (1999).

Dorsey, J.G., et al. "Hydrophobicity estimations by reversed-phase liquid chromatography: Implications for biological partitioning processes," *J. Chromatography A*, 656:485-499(1993).

Escuder-Gilabert, L., et al., "Development of predictive retention-activity relationship models of non-steroidal anti-inflammatory drugs by micellar liquid chromatography: Comparison with immobilized artificial membrane columns," *J. Chromatography B*, 740:59-70 (2000).

Fontenot, J.D., et al. "Synthesis of large multideterminant peptide immunogens using a poly-proline β-turn helix motif," *Peptide Research*, 6(6):330-336 (1993).

Fujita, T., et al. "A new substituent constant, □, derived from partition coefficients," *J. Am. Chem. Soc.*, 86:5175-5180 (1964).

Hilgendorf, C., et al. "Caco-2 Versus Caco-2/HT29-MTX co-cultured cell lines: Permeabilities via diffusion, inside- and outside-directed carrier-mediated transport," *Journal of Pharmaceutical Sciences*, 89(1):63-75 (2000).

Hu, P., et al., "Expression of a recombinant breast tumor-associated mucin fusion protein in *Escherichia coli* exposes the tumor-specific epitope," *Cancer Research*, 53:4920-4926 (1993).

"IAM Chromatography" *Regis Technologies* (1998-2000).

Larhed, A.W., et al., "Diffusion of drugs in native and purified gastrointestinal mucus," *Journal of Pharmaceutical Sciences*, 86(6):660-665 (1997).

Larhed, A.W., et al., "The influence of intestinal mucus components on the diffusion of drugs," *Pharmaceutical Research*, 15(1):66-71 (1998).

Lennernäs, H., "Human perfusion studies," in Oral Drug Absorption: Prediction and Assessment, Dressman, J. and Lennerãs, H., Eds., Marcel Dekker, 106:99-117 (2000).

Lennernäs, H., et al. "A residence-time distribution analysis of the hydrodynamics within the intestine in man during a regional single-pass perfusion with loc-I-gut: In-vivo permeability estimation," *J. Pharm. Pharmacol.*, 49:682-686 (1997).

Leppert, P.S., et al., "Use of everted intestinal rings for in vitro examination of oral absorption," *Journal of Pharmaceutical Sciences*, 83(7):976-981 (1994).

Liu, H., et al., "Predicting drug-membrane interactions by HPLC: Structural requirements of chromatographic surfaces," *Anal. Chem.*, 67:3550-3557 (1995).

Molero-Monfort, M., et al., "Micellar liquid chromatography for prediction of drug transport," *J. Chromatography A*, 870:1-11 (2000).

Molero-Monfort, M.L., et al., "Biopartitioning micellar chromatography: An in vitro technique for predicting human drug absorption," *J. Chromatography B*, 753:225-236(2001).

Ong, S., et al., "Phospholipid immobilization on solid surfaces," *Anal. Chem.*, 66:782-792 (1994).

Ong, S., et al., "Membrane partition coefficients chromatographically measured using immobilized artificial membrane surfaces," *Anal. Chem.*, 67:755-762 (1995).

Ong, S., et al., "Immobilized-artificial-membrane chromatography: measurements of membrane partition coefficient and predicting drug membrane permeability," *J. Chromatography A*, 728:113-128 (1996).

Osiecka, I., et al., "In vitro drug absorption models. I. Brush border membrane vesicles, isolated mucosal cells and everted intestinal rings: Characterization and salicylate accumulation," *Pharmaceutical Research*, 2:284-293 (1985).

Pidgeon, C., et al., "Immobilized artificial membrane chromatography: Supports composed of membrane lipids," *Analytical Biochemistry*, 176:36-47 (1989).

Pidgeon, C., "Solid phase membrane mimetics: Immobilized artificial membranes," *Enzyme Microb. Technol.*, 12:149-150 (1990).

Pidgeon, C., et al., "Immobilized artificial membrane chromatography: Surface chemistry and applications," *Applications of Enzyme Biotechnology*, Kelly, J. and Baldwin, T., Eds., Plenum Press, New York, 201-220 (1991).

Pidgeon C., et al., "Preparation fo Mixed Ligand Immobilized Artificial Membranes for Predicting Drug Binding to Membranes," *Analytical Chemistry* 66:2701-2709 (1994).

Pidgeon, C., et al., "Predicting drug-membrane interactions," *Chemtech*, 38-48 (1995).

Pidgeon, C., et al., "IAM chromatography: An in vitro screen for predicting drug membrane permeability", *J. Med. Chem.*, 38:590-594 (1995).

Pidgeon, C., et al., "Mobile phase effects on membrane protein elution during immobilized artificial membrane chromatography", *J. Chromatography A*, 721:213-230 (1996).

Qui, X., et al., "A $^{31}$P NMR study of immobilized artificial membrane surfaces: Structure and dynamics of immobilized phospholipids," *J. Phys. Chem.*, 97:12399-12407 (1993).

Rhee, D., et al., "Chromatographic surfaces prepared from lyso phosphatidylcholine ligands," *Analytica Chimica Acta*, 297:377-386 (1994).

Rossi, S., et al., "Influence of mucin type on polymer-mucin rheological interactions," *Biomaterials*, 16(14):1073-1079 (1995).

Stewart, B.H. et al., "Use of immobilized artificial membrane chromatography for drug transport Applications," *Journal of Pharmaceutical Sciences*, 87(12):1471-1478 (1998).

Stewart, B.H., et al., "Hydrophobicity of HIV protease inhibitors by immobilized artificial membrane chromatography: application and significance to drug transport" *Pharmaceutical Research*, 15(9):1401-1406 (1998).

Strous, G.J., et al., "Mucin-type glycoproteins " *Critical Reviews in Biochemistry and Molecular Biology* 27:57-92 (1992).

Thornton, D.J., et al., "Separation and identification of mucins and their glycoforms," *Methods in Molecular Biology, Glycoprotein Methods and Protocols: The Mucins*, A.P. Corfield, Ed., Humana Press, Totowa, New Jersey, 125:77-85 (2000).

Tukker, J.J., "In vitro methods for the assessment of permeability" *Oral Drug Absorption: Prediction and Assessment*, Dressman, J. and Lennernäs, H., Eds., Marcel Dekker, Inc., New York, New York, 106:51-73 (2000).

Turowski, M., et al., "Keratin immobilized on silica a new stationary phase for chromatographic modelling of skin permeation," *Journal of Pharmaceutical and Biomedical Analysis*, 15:1325-1333 (1997).

Ussing, H.H., et al., "Active transport of sodium as the source of electric current in the short-circuited isolated frog skin", *Acta Phisiol. Scand.* 23:111-127(1951).

Valko, K., et al., "Rapid-gradient HPLC method for measuring drug interactions with immobilized artificial membrane: Comparison with other lipophilicity measures," *Journal of Pharmaceutical Sciences*, 89(8):1085-1096 (2000).

Wikman, A., et al., "A drug absorption model based on the mucus layer producing human intestinal goblet cell line HT29-H," *Pharmaceutical Research*, 10:843-852 (1993).

Woodley, J., "Bioadhesion: New possibilities for drug administration?," *Clin. Pharmacokinet.*, 40(2):77-84 (2001).

Yang, C., et al., "Immobilized artificial membranes—screens for drug membrane interactions," *Advanced Drug Delivery Reviews*, 23:229-256 (1996).

Zhang, Y., "Immobilized nicotinic receptor stationary phase for on-line liquid chromatographic determination of drug-receptor affinities," *Analytical Biochemistry*, 264:22-25 (1998).

Zotter, S., et al., "Tissue and tumor distribution of human polymorphic epithelial mucin," *Cancer Reviews*, 11-12:55-101 (1988).

\* cited by examiner

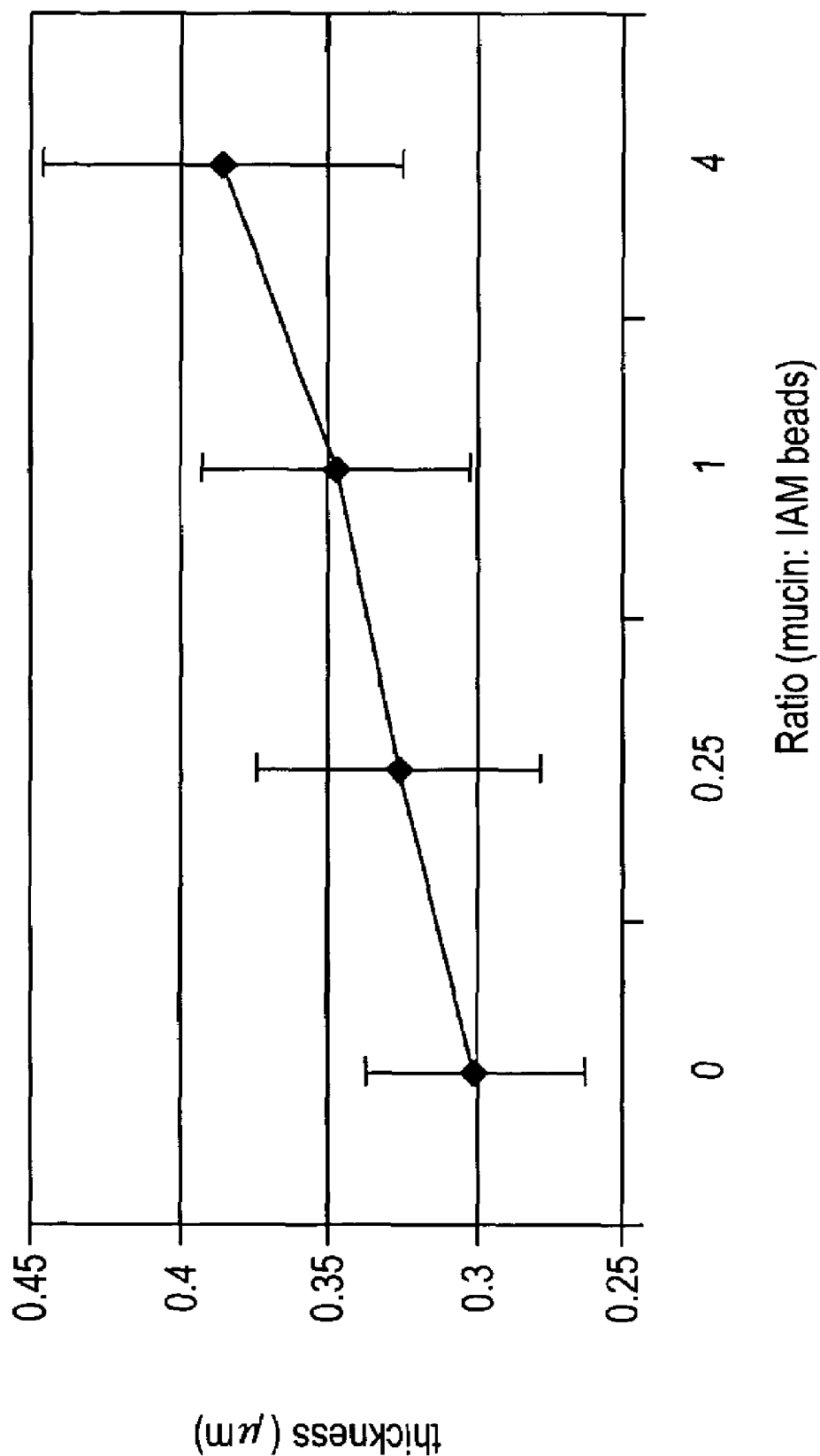

SEQUENCE LISTING

<160> NUMBER OF SEQ ID NOS: 12

<210> SEQ ID NO 1
<211> LENGTH: 20
<212> TYPE: PRT
<213> ORGANISM: Homo sapiens

<400> SEQUENCE: 1

Pro Asp Thr Arg Pro Ala Pro Gly Ser Thr Ala Pro Pro Ala His Gly
 1               5                  10                  15

Val Thr Ser Ala
            20

<210> SEQ ID NO 2
<211> LENGTH: 24
<212> TYPE: PRT
<213> ORGANISM: Homo sapiens

<400> SEQUENCE: 2

Pro Thr Thr Thr Pro Pro Ile Thr Thr Thr Thr Val Thr Pro Thr
 1               5                  10                  15

Pro Thr Pro Thr Gly Thr Gln Thr
            20

<210> SEQ ID NO 3
<211> LENGTH: 17
<212> TYPE: PRT
<213> ORGANISM: Homo sapiens

<400> SEQUENCE: 3

His Ser Thr Pro Ser Phe Thr Ser Ser Ile Thr Thr Thr Glu Thr Thr
 1               5                  10                  15

Ser

<210> SEQ ID NO 4
<211> LENGTH: 16
<212> TYPE: PRT
<213> ORGANISM: Homo sapiens

<400> SEQUENCE: 4

Thr Ser Ser Ala Ser Thr Gly His Ala Thr Pro Leu Pro Val Thr Asp
 1               5                  10                  15

<210> SEQ ID NO 5
<211> LENGTH: 8
<212> TYPE: PRT
<213> ORGANISM: Homo sapiens

<400> SEQUENCE: 5

Thr Thr Ser Thr Thr Ser Ala Pro
 1               5

<210> SEQ ID NO 6
<211> LENGTH: 29
<212> TYPE: PRT
<213> ORGANISM: Homo sapiens

<400> SEQUENCE: 6

Ser Ser Thr Pro Gly Thr Ala His Thr Leu Thr Met Leu Thr Thr Thr
 1               5                  10                  15

```
Ala Thr Thr Pro Thr Ala Thr Gly Ser Thr Ala Thr Pro
             20                  25
```

<210> SEQ ID NO 7
<211> LENGTH: 170
<212> TYPE: PRT
<213> ORGANISM: Homo sapiens

<400> SEQUENCE: 7

```
Ser Pro Phe Ser Ser Thr Gly Pro Met Thr Ala Thr Ser Phe Gln Thr
 1               5                  10                  15

Thr Thr Thr Tyr Pro Thr Pro Ser His Pro Gln Thr Thr Leu Pro Thr
             20                  25                  30

His Val Pro Pro Phe Ser Thr Ser Leu Val Thr Pro Ser Thr Gly Thr
         35                  40                  45

Val Ile Thr Pro Thr His Ala Gln Met Ala Thr Ser Ala Ser Ile His
     50                  55                  60

Ser Thr Pro Thr Gly Thr Ile Pro Pro Thr Thr Leu Lys Ala Thr
 65                  70                  75                  80

Gly Ser Thr His Thr Ala Pro Pro Met Thr Pro Thr Thr Ser Gly Tyr
                 85                  90                  95

Ser Gln Ala His Ser Ser Thr Ser Thr Ala Ala Lys Thr Ser Thr Ser
                100                 105                 110

Leu His Ser His Thr Ser Ser His His Pro Glu Val Thr Pro Thr
                115                 120                 125

Ser Thr Thr Thr Ile Thr Pro Asn Pro Thr Ser Thr Gly Thr Ser Thr
130                 135                 140

Pro Val Ala His Thr Thr Ser Ala Thr Ser Ser Arg Leu Pro Thr Pro
145                 150                 155                 160

Phe Thr Thr His Ser Pro Pro Thr Gly Ser
                165                 170
```

<210> SEQ ID NO 8
<211> LENGTH: 22
<212> TYPE: PRT
<213> ORGANISM: Homo sapiens

<400> SEQUENCE: 8

```
Thr Thr Ala Ala Pro Pro Thr Pro Ser Ala Thr Thr Pro Ala Pro Pro
 1               5                  10                  15

Ser Ser Ser Ala Pro Gly
             20
```

<210> SEQ ID NO 9
<211> LENGTH: 41
<212> TYPE: PRT
<213> ORGANISM: Homo sapiens

<400> SEQUENCE: 9

```
Thr Ser Cys Pro Arg Pro Leu Gln Glu Gly Thr Pro Gly Ser Arg Ala
 1               5                  10                  15

Ala His Ala Leu Ser Arg Arg Gly His Arg Val His Glu Leu Pro Thr
             20                  25                  30

Ser Ser Pro Gly Gly Asp Thr Gly Phe
         35                  40
```

<210> SEQ ID NO 10
<211> LENGTH: 15

-continued

```
<212> TYPE: PRT
<213> ORGANISM: Homo sapiens

<400> SEQUENCE: 10

Val Gly His Gln Ser Val Thr Pro Gly Glu Lys Thr Leu Thr Ser
 1               5                  10                  15

<210> SEQ ID NO 11
<211> LENGTH: 28
<212> TYPE: PRT
<213> ORGANISM: Homo sapiens

<400> SEQUENCE: 11

Ser Gly Leu Ser Glu Glu Ser Thr Thr Ser His Ser Ser Pro Gly Ser
 1               5                  10                  15

Thr His Thr Thr Leu Ser Pro Ala Ser Thr Thr Thr
            20                  25

<210> SEQ ID NO 12
<211> LENGTH: 28
<212> TYPE: PRT
<213> ORGANISM: Homo sapiens

<400> SEQUENCE: 12

Ser Gly Leu Ser Gln Glu Ser Thr Thr Phe His Ser Ser Pro Gly Ser
 1               5                  10                  15

Thr His Thr Thr Leu Ser Pro Ala Ser Thr Thr Thr
            20                  25
```

US 7,659,240 B2

MUCIN IMMOBILIZED CHROMATOGRAPHY

CROSS REFERENCE TO RELATED APPLICATIONS

This application claims priority to U.S. Provisional Patent Application 60/348,184, filed Jan. 14, 2002, the content of which is incorporated by reference.

TECHNICAL FIELD OF THE INVENTION

The invention relates to an in vitro mucin immobilized chromatography (MIC) model to estimate drug permeability coefficients. More particularly, the present invention provides compositions for MIC media and methods for preparing MIC media. In addition, the invention provides methods to estimate in vitro drug permeability coefficients using MIC media, including, inter alia column or batch chromatography or high-throughput screening (HTS) analyses. The present invention further relates to methods for estimating drug permeability coefficients in individuals, including healthy and diseased individuals using the in vitro MIC model. The present invention also relates to methods for emulating absorption processes in the digestive system, and in other tissues and organs comprising a mucosal layer.

BACKGROUND OF THE INVENTION

Oral drug administration is a noninvasive route of drug delivery for the treatment or prevention of diseased states in animals. The success of oral drug administration depends upon many factors, one of which is the degree of bioavailability of the drug. Bioavailability accounts for "the rate and extent to which the active ingredient or active moiety is absorbed from a drug product and becomes available at the site of action." 21 C.F.R. § 320.1 (2000). In general, a host of biological factors affect bioavailability, including the pharmacokinetic behavior of the drug, drug formulation, site of administration, formulation and dosage form, and the physiological state of the patient.

In oral drug administration, one of the critical steps in determining bioavailability is the transportation and absorption of the drug across the various cell membranes comprising the intestinal mucosa (Lennernäs, H., "Human Perfusion Studies" in *Oral Drug Absorption: Prediction and Assessment*, Dressman, J. and Lennernäs, H., Eds., Marcel Dekker, 106, 99-117 (2000)). An important variable in calculating the extent of absorption is the effective permeability, $P_{eff}$, because $P_{eff}$ is the rate-limiting step in the absorption process (Stein, W. D., *Transport and Diffusion across Cell Membranes*, Academic Press, Inc., Orlando, Fla., 1986).

Drug transport proceeds either by carrier-mediated transport, transcellular transport or passive diffusion mechanisms. Most orally-administered drugs are absorbed by passive diffusion mechanisms. For drugs that are absorbed by passive diffusion, there are a number of in vivo and in vitro intestinal absorption models that can be used to estimate the absorption of potential oral drug candidates during initial drug screening tests.

In order to accurately measure $P_{eff}$, Lennerns et al. developed an in vivo human single-pass intestinal perfusion model to measure membrane transport. A large number of drugs belonging to several pharmacological classes were measured using this model, including cardiovascular system agents, nonsteroidal anti-inflammatory drugs (NSAIDs), central nervous system (CNS) agents, anti-infective agents, urinary tract system agents, and gastroenterological agents. These data serve as a guideline for classifying drug substances based on their aqueous solubility and intestinal permeability under the Biopharmaceutical Classification System (BCS) (fda.gov/cder/guidance/3618fnl.htm on the world wide web). The in vivo data generated by this method provide accurate $P_{eff}$ values, and are useful for comparative studies with in vitro data; however, the measurement of bioavailability by the human intestinal perfusion model or by other in vivo methods is impractical for HTS.

To this end, a number of in vitro absorption models have been developed to calculate and predict the parameters involved in drug absorption more quickly than in vivo models. These include the isolated intestinal cell model (Osiecka et al., Pharm. Res. 2, 284-293 (1985)), the everted intestinal ring model (Leppert and Fix, J. Pharm. Sci. 83, 976-981 (1994)), the everted intestinal sac model (Barthe et al., J. Drug Metab. Pharmocokinet. 23, 313-323 (1998)), the Ussing chamber model (Ussing and Zerahn, Acta. Phisiol. Scand. 23, 110-127 (1951)), the octanol-water partitioning model (Fujita et al., J. Am. Chem. Soc. 86, 5175-5180, (1964)), and the Caco-2 cell model (Artursson and Karlsson, Biochem. Biophy. Res. Comm. 175, 880-885 (1991)). Other models specifically utilizing chromatography methods include octadecyl-reversed phase chromatography (ODS) (Dorsey and Khaledi, J. Chromatography A 656, 485-499 (1993)), immobilized artificial membranes (IAM) (Yang et al., Advanced Drug Delivery Reviews 23, 229-256 (1996)), and micellar liquid chromatography (MLC) (Molero-Monfort et al., J. Chromatography A 870, 1-11 (2000)).

The accuracy of correlation of in vitro drug absorption values to those obtained by in vivo methods varies according to the model used. For example, one widely used in vitro model, the human intestinal Caco-2 cell line, emulates the intestinal cellular epithelium in humans very well (Artursson and Karlsson, *Biochem. Biophy. Res. Comm.* 175, 880-885 (1991)). Other in vitro models that may be used include the human intestinal epithelial cell lines, HT29-H and a co-culture of Caco-2 and HT29-MTX, wherein the outer surface of the cells contain a secreted mucin layer (Wikman et al., *Pharmaceutical Research* 10, 6, 843-852 (1993); Hilgendorf et al., *J. Pharm. Sci.* 89, 1, 63-75 (2000)). However, the experimental use of cell lines require costly and continuous maintenance programs to ensure cell viability. As a result, high performance liquid chromatography (HPLC) models, such as immobilized artificial membranes (IAM) and micellar liquid chromatography (MLC), which are experimentally easier to use than cell culture models, have been developed and shown to predict drug absorption with reliability and accuracy comparable to that of the Caco-2 cell model (Stewart et al., *Pharm. Res.* 15, 1401-1406 (1998)).

IAM creates mechanically stable chromatographic surfaces that mimic cell membranes (Pidgeon et al., *Applications of Enzyme Biotechnology*, 201-220 (1991)). The cell membrane structures are modeled after liposomes (Bangham et al., *Methods Membr. Biol.* 1, 1-68 (1974)) and are created by covalent attachment of the membrane-forming lipids, largely phospholipids, to a chromatographic surface.

U.S. Pat. No. 4,927,879 discloses a method for forming an IAM by the covalent attachment of amphiphilic cyclic dicarboxylic anhydrides to silica. The attached molecules form a tightly packed arrangement on the surface of the support to prevent additional nucleophilic reactions from occurring at these sites. U.S. Pat. No. 4,931,498 describes compositions and methods used to immobilize the membrane-forming lipids to silica supports.

Unlike IAM models, MLC models comprise a reversed stationary phase in combination with a surfactant solution mobile phase, wherein the surfactant concentration in the mobile phase exceeds its critical micelle concentration (CMC) (Escuder-Gilabert et al., *J. Chromatography B* 740, 59-70 (2000)). The surfactant, polyoxyethylene lauryl ether (Brij-35), adsorbs to the hydrophobic stationary phase and behaves as the polar membrane region of a cell. If supplemented with saline, the Brij-35 mobile phase further acts as an extracellular fluid. Like IAM models, MLC models predict the partitioning behavior of small molecule absorption into the lipid bilayers of the cell membrane.

IAM and MLC are currently being used to predict oral drug absorption and bioavailability. However, IAM and MLC methods are limited because they only model one part of the absorptive process, that is, the passive diffusion across the lipid bilayer. IAM and MLC do not model the initial absorption process across the epithelial mucosa, which is critical for drug absorption.

The epithelial mucosa, or mucus, is a hydrogel comprising inter alia, mucins, lipids, proteins, DNA, RNA and carbohydrates. The epithelial mucosa covers all epithelial surfaces, including respiratory, buccal, gastrointestinal, reproductive and urinary tract surfaces and coats the plasma membrane. Mucus functions to protect the cell surface from harmful extracellular molecules, and to regulate cellular interactions and molecular uptake that occur between the cell and its environment (Braybrooks et al., *J. Pharm. Pharmac.* 27, 508-515 (1975); Larhed et al., *J. Pharm. Sci.* 86, 660-665 (1997); Larhed et al., *Pharm. Res.* 15, 66-71 (1998)).

Mucins, the major components of mucus, are a family of high molecular weight glycosylated proteins that impart viscous and viscoelastic properties on mucus (Strous and Dekker, *Critical Reviews in Biochemistry and Molecular Biology*, 27, 57-92 (1992)). Differences in the type, level, and pattern of glycosylation in mucins is often altered in certain diseased states, including cancer (see, e.g., (Bhavanandan, *Glycobiology* 1, 493-503 (1991); Finn et al., U.S. Pat. No. 5,827,666). Mucins are primarily responsible for determining whether a substance, such as a drug, crosses the mucosal layer to enter the cells underlying the mucosal layer.

To date, in vitro models fail to provide a fast and convenient means to emulate the outer layer of the cell membrane and the cellular mucosa in order to investigate drug absorption. It would therefore be desirable to develop a chromatography model that measures the initial absorption process of a drug across a mimetic mucosal surface in order to obtain a more accurate representation of drug absorption across epithelial mucosa. Such a model would be particularly useful for modeling gastrointestinal drug absorption after oral administration. In addition, it would be desirable to develop a fast, cost efficient method to estimate drug absorption for HTS in both healthy and diseased states.

SUMMARY OF THE INVENTION

The present invention is directed to an in vitro mucin immobilized chromatography model (MIC) that may be used to determine drug permeability coefficients across mucosal membranes. The invention simulates the initial step in the fate of the drug, that is, the interaction of the drug with mucin components and the cell membrane of the epithelial mucosa.

The present invention provides compositions for MIC media and methods for preparing MIC media. In addition, the invention provides methods to estimate in vitro drug permeability coefficients using MIC media, including inter alia column or batch chromatography or HTS analyses. The present invention further provides methods for estimating drug permeability in individuals, including healthy and diseased individuals using the in vitro MIC model. The present invention also relates to methods for emulating absorption processes in the digestive system, and in other tissues and organs comprising a mucosal layer.

The MIC media comprise a mucin-type protein or a mucin-type peptide non-covalently immobilized to a solid support matrix, wherein said solid support matrix is surface modified with an amphiphlic molecule. The MIC media may comprise one or more different types of mucin-type proteins or mucin-type peptides. The MIC media may further comprise one or more components of the mucus layer, including a lipid, a non-mucin protein, DNA, RNA, or a carbohydrate. According to another embodiment of the present invention, the composition may comprise both a mucin-type protein and a mucin-type peptide. The mucin-type protein or mucin-type peptide may be derived from a secreted mucin or a membrane-bound mucin. The MIC media may comprise a combination of secreted and membrane-bound mucins.

The mucin-type proteins of the MIC media may have a variety of types and levels of glycosylation. The mucin-type protein may contain threonine and serine amino acid residues that are fully O-linked glycosylated, partially O-linked glycosylated, or non-glycosylated at the hydroxyl group of each serine or threonine amino acid side chain. The hydroxyl group may be glycosylated with a carbohydrate selected from the group consisting of monosaccharides, disaccharides, oligosaccharides, and polysaccharides. Preferably, an oligosaccharide is selected from the group consisting of Gal $\beta$(1-3)-GalNAc $\alpha$(1-O)—, Gal $\beta$(1-3)-[GlcNAc $\beta$(1-6)]-GalNAc $\alpha$(1-O)—, GlcNAc $\beta$(1-3)-GalNAc $\alpha$(1-O)—, GlcNAc $\beta$(1-3)-[GlcNAc $\beta$(1-6)]-GalNAc $\alpha$-(1-O)—, GalNAc $\alpha$(1-3)-GalNAc $\alpha$-(1-O)—, and Gal $\beta$(1-3)-[Gal $\beta$(1-6)]GalNAc $\alpha$(1-O)—. In another preferred embodiment, the disaccharide is Gal$\beta$(1-3)GalNAc $\alpha$-. In another preferred embodiment, the monosaccharide is GalNAc.

Similarly, mucin-type proteins may be N-linked glycosylated at asparagine amino acid residues found in the protein chain. The mucin-type protein may contain asparagine amino acid residues that are fully N-linked glycosylated, partially N-linked glycosylated, or non-glycosylated at each amide group of asparagine that is part of the sequence of amino acids Asn-X-Ser or Asn-X-Thr, wherein X is any amino acid other than proline and aspartic acid. The amide nitrogen may be glycosylated with a carbohydrate selected from the group consisting of monosaccharides, disaccharides, oligosaccharides, and polysaccharides. Preferably, the N-linked side chain is glycosylated with a hexasaccharide, $GlcNAc_3Man_3$.

In another aspect of the present invention, the mucin-type peptide is non-glycosylated. In another embodiment, the mucin-type peptide, whether glycosylated or not, is an epitope associated with mucin from either malignant or normal cells.

This invention also relates to a MIC composition wherein the mucin-type protein or mucin-type peptide is derived from the epithelial cell surface coatings of the gastrointestinal (GI) tract, mouth, eye, trachea, lungs, salivary glands, sweat glands, breast, reproductive tract (e.g., vagina), pancreatic duct, gall bladder or urinary tract (e.g., urethra or vagina). The mucin-type protein or mucin-type peptide may be derived from normal or cancerous epithelial cells. Another embodiment of the present invention is a MIC composition wherein the mucin-type protein or mucin-type peptide is derived from the transmembrane domain of mucins from epithelial cells of the GI tract, mouth, eye, trachea, lungs, salivary glands, sweat glands, breast, reproductive tract, pancreatic duct, gall bladder or urethra.

In a further embodiment, the present invention relates to a MIC media comprising a mucin-type protein or mucin-type peptide that is derived from a mammalian mucin. Said mammalian mucin may be selected from the group consisting of human, ape, monkey, rat, pig, dog, rabbit, cat, cow, horse, mouse, rat and goat. In yet a further embodiment, the present invention relates to a MIC media comprising a mucin-type protein or mucin-type peptide that comprises at least one tandem repeat sequence selected from the group consisting of SEQ ID NOS:1-12. In another embodiment, a mucin-type peptide is 5 to 50 amino acids in length and a mucin-type protein is greater than 50 amino acids in length.

In another embodiment, the invention provides a MIC media comprising a solid support matrix that comprises an inorganic molecule, a polymer, or a copolymer. The inorganic molecule may be selected from silicates, aluminas, hydroxyapatites, zeolites, germanates, phosphates or a mixture thereof. In a preferred embodiment, the inorganic molecule is a functionalized silicate. In a more preferred embodiment, the functionalized silica gel is selected from the group consisting of 3-aminopropyl silica, 1-allyl silica, 3-(3,4-cyclohexyldiol) propyl, 3-(diethylenetriamino)propyl, 4-ethyl benzenesulfonamide, 3-mercaptopropyl, propionyl chloride, 3-(2-succinic anhydride)propyl, and 3-(ureido)propyl.

In another preferred embodiment, the solid support matrix is a polymer selected from the group consisting of agarose, dextran, polystyrene, polyvinyl alcohol, polymethylacrylate, polymethylmethacrylate and acrylamides. In another preferred embodiment, the solid support matrix is a copolymer selected from the group consisting of polyethyleneglycol-co-polystyrene, polystyrene-co-divinylbenzene, sulfonated styrene-divinylbenzene, polyvinylchloride-co-vinylacetate, bis-acrylamide-azalactone, N-vinylpyrrolidone-co-divinylbenzene, polyethylene-co-butyl methacrylate, poly(lactic-co-glycolic acid), lignin-cresol copolymers, dextran-agarose copolymers, glycidyl methacrylate-ethylene dimethacrylate copolymers, poly(lactide-co-caprolactone) and polyacrylic copolymers.

In another aspect, the invention provides a MIC media comprising an amphiphilic molecule covalently attached to the surface of a solid support matrix. In one embodiment, the molecule comprises an epithelial cell membrane constituent. In a preferred embodiment, the amphiphilic molecule is selected from the group consisting of phospholipids, phosphoglycerides, spingolipids, prostaglandins, saturated fatty acids, unsaturated fatty acids, and soaps. Preferably, the amphiphilic molecule is a phospholipid. In a more preferred embodiment, the amphiphilic molecule is phosphatidyl choline.

The present invention provides a MIC media in which the mucin-type proteins and mucin-type peptides are prepared by isolation from a biological source or by recombinant DNA methods, synthetic chemical routes, or a combination of any of these methods.

Recombinant DNA methods include expressing the protein or peptide of interest from a host cell that comprises a nucleic acid molecule comprising a nucleic acid sequence encoding the protein or peptide of interest. The host cell may comprise a vector comprising the nucleic acid sequence. The vector may further comprise an expression control sequence operably linked to the nucleic acid sequence. In a preferred embodiment, the nucleic acid sequence encodes an amino acid sequence selected from the group consisting of a mucin-type protein and a mucin-type peptide. The mucin-type peptide may comprise a mucin epitope.

The host cell may be a prokaryotic or a eukaryotic cell. In a preferred embodiment, the prokaryotic cell is an *E. coli* cell. In another preferred embodiment, the eukaryotic cell may be selected from the group consisting of yeast, insect, and mammalian cells.

Another aspect of the present invention is to provide a method for the preparation of a chromatography medium. The method comprises providing a solution of a mucin-type protein or peptide and mixing the solution with a solid support matrix, wherein the matrix surface is modified with an amphiphilic molecule, under conditions in which the protein or peptide forms a non-covalent interaction with the matrix. In a preferred embodiment, the mucin-type protein or mucin-type peptide may be dissolved in a solvent. In a more preferred embodiment, the solvent may be acetone, Dulbecco phosphate buffered saline (DPBS) optionally comprising a non-ionic surfactant such as Brij-35. The solvent may be any other suitable solvent as well. The mixture may be washed and/or dried before use. In one embodiment, the mixture is dried by evaporation. The evaporating step may be evaporation by air or by rotoevaporation, wherein both heat and vacuum are applied.

The MIC media may be used in any method, including, inter alia, batch chromatography or column chromatography. Column chromatography includes liquid chromatography, high performance liquid chromatography, and fast performance liquid chromatography. The MIC media may also be used to coat a slide or plate for thin layer chromatography. In another embodiment, the MIC media may be used to coat a multi-well plate for HTS or other high-throughput analyses.

Another aspect of the present invention is to provide in vitro methods for estimating drug absorption through the mucus layer. This method comprises determining an effective permeability coefficient ($P_{eff}$) for a drug compound using MIC media.

In one aspect, the invention provides a method of estimating the permeability coefficient of one or more drugs by contacting the drug with the MIC media, measuring the degree of binding of the drug on the MIC media and estimating the drug permeability coefficient. In a preferred embodiment, the contacting step is performed by loading the drug on a column comprising the MIC media and the measuring step is performed by measuring the retention time of the drug on the column. In one embodiment, the drug permeability coefficient is estimated for a single drug. In another preferred embodiment, permeability coefficients of a number of drugs are measured either sequentially, by contacting each drug with the MIC media one by one and measuring binding of the drug to the media, or simultaneously, by contacting a mixture of more than one drug with the MIC media and measuring binding of the drug to the media. In another embodiment, the MIC media comprises types and/or amounts of mucin-type protein or mucin-type peptide to mimic the mucus layer in a specific cell, tissue or organ. These include the mucus layer of the GI tract, eye, trachea, lungs, salivary glands, sweat glands, breast, reproductive tract, pancreatic duct, gall bladder or urinary tract.

In another aspect, the method may be used to compare the relative permeability of one or more drugs to each other or to drugs having a known permeability.

The method comprises contacting the MIC media with a drug of interest and measuring the degree of binding of the drug to the MIC media, then comparing the degree of binding to that measured for one or more other drugs. The other drug may be one having an unknown drug permeability coefficient or may be one having a known drug permeability coefficient. The method may be used to determine whether the drug of interest has a greater or lesser relative permeability compared to the other drug. Further, by comparing the drug of interest to one or more other drugs having a known permeability coefficient, one may estimate the permeability coefficient for the drug of interest. The degree of binding may be measured sequentially or simultaneously. The degree of binding may be determined using column chromatography or by batch chromatography. See Example 5.

Another embodiment of the invention is to provide a method for estimating effective permeability coefficients of one or more drugs in two or more physiological states by changing the amount and/or type of mucin-type protein or mucin-type peptide in the MIC media. In one preferred embodiment, the MIC media comprises types and/or amounts of mucin-type proteins or mucin-type peptides that mimic the mucus layer in a healthy state or in a diseased states. In another embodiment, the method provides a method for estimating effective permeability coefficients of one or more drugs in two or more physiological states by changing the mobile phase of the media. In a preferred embodiment, the pH, osmolarity and/or surfactant concentration or type is altered to mimic a particular physiological state.

The MIC media may be used to mimic the healthy or diseased state of any mucosal layer, including the gastrointestinal tract, reproductive tract, urinary tract, eye, mouth, salivary glands, pancreatic glands, sweat glands or gall bladder. In a preferred embodiment, the diseased state is an epithelial cell cancer.

In another embodiment, the different physiological states are different developmental stages, e.g., infant, child, adolescent and adult. In another embodiment, the different physiological states may be mucosal layers from different cells, tissues, or organs. For example, one may compare estimated drug absorption in the mouth, gastrointestinal tract and reproductive tract to determine the best method of administration.

A further embodiment of this invention is to provide a method for emulating an absorption process in a system comprising more than one epithelial mucosal layer. The method comprises estimating drug permeability coefficients using a series of chromatography columns each having a different amount and/or type of a mucin-type protein, mucin-type peptide, or combination thereof immobilized to a chromatography medium, wherein the different amounts and/or types of mucin-type proteins or mucin-type peptides mimic the different mucus linings in the system. In a preferred embodiment, the mobile phase may be altered to mimic the different extracellular fluids in the system. In a preferred embodiment, the system is the digestive system.

Another embodiment of the present invention is a kit comprising the MIC media. The kits may be used to estimate absorption of one or more drugs.

Another embodiment of the present invention comprises a method for using MIC in HTS.

BRIEF DESCRIPTION OF THE DRAWINGS

FIG. 4 illustrates the thickness of the mucin-phosphatidyl choline layer on the solid matrix as measured by confocal microscopy. See Example 3.

DETAILED DESCRIPTION OF INVENTION

Definitions

Figure 1:
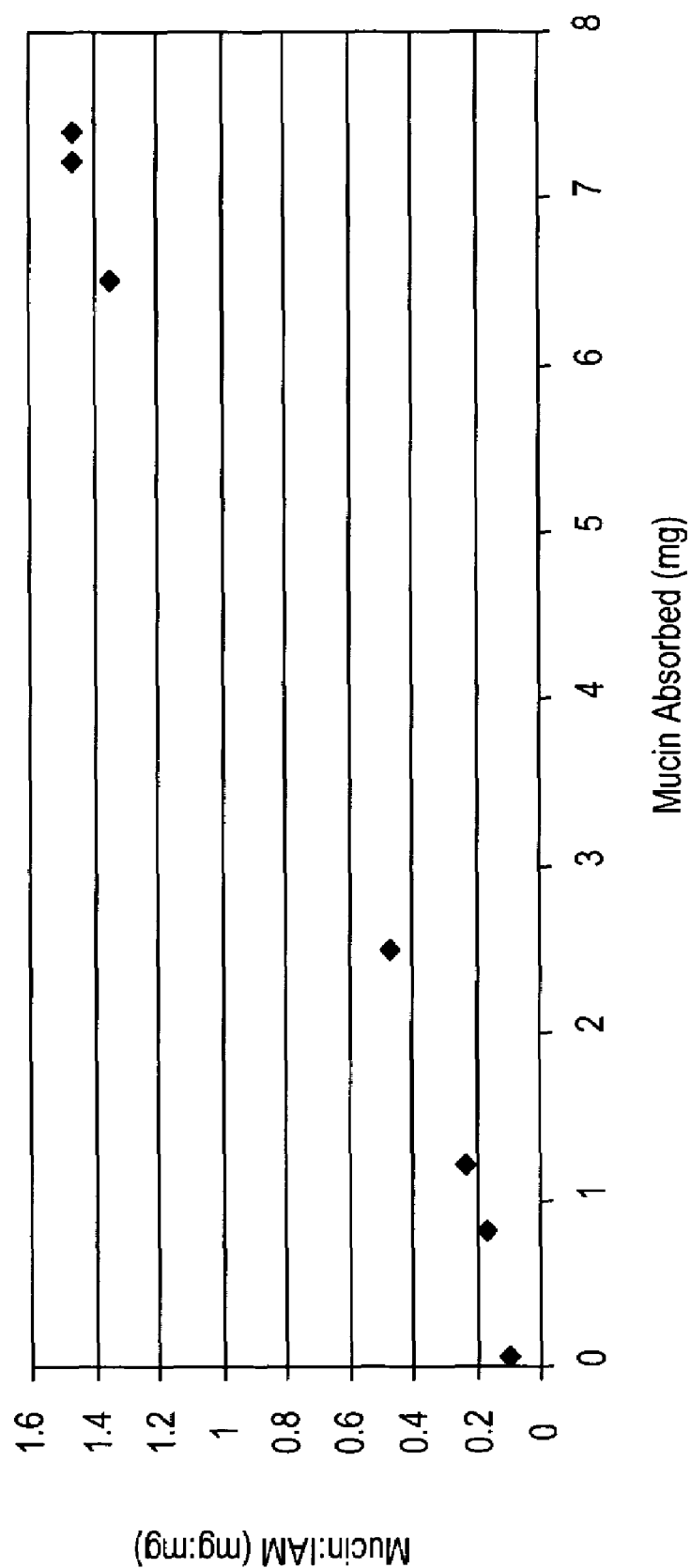
FIG. 1 illustrates an optimization plot between the amount of mucin absorbed to IAM beads versus the weight ratio of mucin to IAM beads. See Example 1.

Unless otherwise defined herein, scientific and technical terms used in connection with the present invention shall have the meanings that are commonly understood by those of ordinary skill in art. Further, unless otherwise required by context, singular terms shall include pluralities and plural terms shall include the singular. Generally, nomenclatures used in connection with, and techniques of, column chromatography, recombinant DNA methods, peptide and protein chemistries, and conjugation chemistries described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989); Ausubel et al., *Current Protocols in Molecular Biology,* Greene Publishing Associates (1992, and Supplements to 2002); Hermanson, *Bioconjugate Techniques,* Academic Press, San Diego, Calif. (1996); *Solid-Phase Peptide Synthesis,* G. B. Fields, Ed., 1st ed., Academic Press, New York, 289 (1997); *Handbook of Chromatography: General Data and Principles Volume II,* G. Zweig and J. Sherma, Eds., CRC Press, Boca Raton, Fla. (1972); each of which is incorporated herein by reference in its entirety.

The following terms, unless otherwise indicated, shall be understood to have the following meanings:

Chromatography medium is defined as either a liquid or a solid stationary phase used in separation techniques.

Solid support matrix is any solid stationary phase comprised of organic or inorganic molecules, polymers, copolymers or combinations thereof.

An inorganic molecule as used herein refers to any suitable inorganic molecule that may be used as a solid support matrix for MIC media. In a preferred embodiment, the inorganic molecule is selected from silicates, aluminas, hydroxyapatites, zeolites, germanates or phosphates.

A polymer refers to a molecule having a molecular weight of approximately 5,000 or greater, which is composed of monomer units of less than 5,000 molecular weight covalently bonded together.

The term copolymer comprises a polymer having more than one monomer unit per chain. The sequence of monomer units within the overall composition of a copolymer can be alternating, block, or statistical (Odian, *Principles of Polymerization*, 3rd Ed., 142-149 (1991)).

An amphiphilic molecule is a molecule having a polar domain and a nonpolar domain.

The term mucus layer is defined as a lining on an epithelial cell surface of the GI tract, eye, trachea, lungs, salivary glands, sweat glands, breast, reproductive tract, pancreatic duct, gall bladder or urinary tract. The mucus lining may be derived from a normal cell, tissue or organ, or from a cancerous cell, tissue or organ. The mucus layer is comprised of a number of components including mucins, lipids, proteins, DNA, RNA and carbohydrates.

The term glycoprotein is defined as a molecule comprising a carbohydrate moiety and a proteinaceous moiety. A comprehensive database of glycoproteins and their O-linked glycosylation sites from a variety of species is available through the Center For Biological Sequence Analysis at cbs.dtu.dk/databases/OGLYCBASE/Oglyc.base.gz on the world wide web.

Mucin refers to a class of high molecular weight glycosylated proteins that are either secreted or membrane-bound and that form a viscous gel covering epithelial cells. Secreted mucins refer to proteins that are not kinked via a transmembrane region to the cells. They are synthesized by epithelial cells that are stored intracellularly prior to being transported to the apical side of the cells where they are released into the extracellular space to form a part of the mucus layer. Secreted mucins form oligomeric, crosslinked molecular aggregates or viscoelastic gels. Membrane-bound mucins refer to integral membrane proteins synthesized in epithelial cells that are not stored intracellularly prior to being transported to apical plasma membrane. Membrane-bound mucins are typically monomeric and contain protein domains associated with signaling processes.

Glycosylation refers to the process of adding carbohydrate moieties to protein side-chains. O-linked glycosylation occurs at the hydroxyl group of threonine or serine and N-linked glycosylation occurs at the amide nitrogen of asparagine. Both O-linked and N-linked carbohydrate moieties can be monosaccharides, disaccharides, oligosaccharides, or polysaccharides. A monosaccharide may be either an aldose or a ketose and is classified as a triose, tetrose, pentose, hexose, or heptose depending upon the number of carbons in the carbohydrate moiety. Examples of monosaccharides include glyceraldehyde, ribose, xylose, arabinose, glucose, galactose, mannose, ribulose, fructose, glucopyranose, ribofuranose, and fructofuranose. A disaccharide is two covalently linked monosaccharides. Examples of disaccharides include maltose, lactose, and sucrose. An oligosaccharide is defined as 3-9 covalently-linked monosaccharides, which are O-linked or N-linked to each other. A polysaccharide is defined as a polymer of approximately greater than about ten monosaccharide residues linked glycosidically in branched or unbranched chains. Examples of a polysaccharide include amylose, amylopectin, glycogen, cellulose, and starch.

A mucin-type protein or mucin-type peptide is fully O-linked glycosylated when each serine and threonine residue in the tandem repeat region in a specific mucin-type protein molecule or mucin-type peptide molecule is O-linked glycosylated. Similarly, a mucin-type protein or mucin-type peptide is fully N-linked glycosylated when each asparagine residue in the tandem repeat region and in the consensus sequence of amino acids Asn-X-Ser or Asn-X-Thr, wherein X is any amino acid other than proline and aspartic acid, is N-linked glycosylated. A mucin-type protein or mucin-type peptide is partially O-linked glycosylated when between 10-90% serine and threonine residues are O-linked glycosylated in the tandem repeat region or when between 10-90% asparagine residues are N-linked glycosylated in the tandem repeat region. A mucin-type protein or mucin-type peptide is non-glycosylated when no serine or threonine residue is O-linked glycosylated or when no asparagine residue is N-linked glycosylated.

A peptide is defined as two to 50 amino acids and/or imino acids connected to one another.

A polypeptide is defined as a chain of greater than 50 amino acids and/or imino acids connected to one another. In general, peptides and polypeptides are linked by peptide bonds. However, other bonds that may be substituted for peptide bonds are known in the art. Peptides and polypeptides may be composed of naturally or non-naturally occurring amino acids or of amino or imino acid substitutes known in the art.

A protein is a large macromolecule composed of one or more polypeptide chains.

For the purposes of this invention, the term "mucin-type protein" or "mucin-type protein that is derived from a mucin" refers to a protein that is greater than 50 amino acids in length and that has an amino acid sequence the same or similar to a mucin protein. Mucin-type proteins may be isolated from a biological source, synthesized recombinantly, synthesized by chemical coupling of amino acids, peptide or polypeptide units, or formed by combining any of these through chemical coupling.

The term "mucin-type peptide" or "mucin-type peptide that is derived from a mucin" refers to a molecule or macromolecule that is equal to or less than 50 amino acids in length and that has an amino acid sequence the same as or similar to all or a part of a mucin protein. Mucin-type peptides may comprise one or more tandem repeat regions. Mucin-type peptides are generally synthesized by chemical methods but can also be isolated from biological sources or synthesized by recombinant methods.

The term covalent bond refers to a region of relatively high electron density between nuclei which arises partly by shared-electrons and have average bond energies on the order of 200-400 kJ/mol. Non-covalent bonds are all other bonds not classified as covalent bonds and comprise ionic bonds, hydrogen bonds, Van der Waals interactions and hydrophobic interactions and have bond energies on the order of 2-50 kJ/mol.

An epitope or single antigenic determinant is either a group of amino acids on a protein surface or groups of sugar residues in a carbohydrate which is responsible for combining with the antibody or T-cell receptor combining site.

An amino acid sequence is similar to a reference amino acid sequence when it has at least 70% sequence identity to the reference amino acid sequence.

In a preferred embodiment, the sequence identity is at least 75%, 80%, 85% or 90%. In a more preferred embodiment, the amino acid sequence is at least 95%, 96%, 97%, 98% or 99% identical to the reference sequence.

The term immobilized refers to a molecule that reaches equilibrium upon being absorbed or affixed to a chromatography medium, wherein no more that 2% of the total amount is washed off during each experimental analysis.

Compositions for Mucin Immobilized Chromatography

One embodiment of the invention is drawn to a composition that can be used for MIC. In one embodiment, the composition comprises a protein non-covalently immobilized to a solid support matrix, wherein said protein is a mucin-type protein or mucin-type peptide and the solid support matrix comprises a surface with covalently attached amphiphilic molecules.

The MIC composition comprises a solid support matrix that is comprised of an inorganic molecule, a polymer, or a copolymer. In one embodiment, the solid support matrix is an inorganic molecule that is selected from the group consisting of silicates, aluminas, hydroxyapatites, zeolites, germanates or phosphates. In a preferred embodiment, the inorganic is a functionalized silica gel. In a more preferred embodiment, the functionalized silica gel is 3-aminopropyl silica, 1-allyl silica, 3-(3,4-cyclohexyldiol)propyl, 3-(diethylenetriamino) propyl, 4-ethyl benzenesulfonamide, 3-mercaptopropyl, propionyl chloride, 3-(2-succinic anhydride)propyl, and 3-(ureido)propyl.

In another preferred embodiment, the solid support matrix is a polymer selected from the group consisting of agarose, dextran, polystyren, polyvinyl alcohol, polymethylacrylate, polymethylmethacrylate, and acrylamides. In another embodiment, the solid support matrix is a copolymer selected from the group consisting of polyethyleneglycol-co-polystyrene, polystyrene-co-divinylbenzene, sulfonated styrene-divinylbenzene, polyvinylchloride-co-vinylacetate, bis-acrylamide-azalactone, N-vinylpyrrolidone-co-divinylbenze, polyethylene-co-butyl methacrylate, poly(lactic-co-glycolic acid), lignin-cresol copolymers, dextran-agarose copolymers, glycidyl methacrylate-ethylene dimethacrylate copolymers, poly(lactide-co-caprolactone) and polyacrylic copolymers.

The invention also provides an amphiphilic molecule covalently attached to the surface of a solid support matrix. The amphiphilic molecule can bind to the surface of the matrix and present a hydrophilic domain that extends away from the matrix surface. Without seeking to be bound by any theory, it is believed that the interaction of the hydrophobic domain of the amphiphilic molecule with the matrix forms a hydrophobic matrix for non-covalent entrapment of molecules, particularly mucin-type proteins and/or mucin-type peptides.

In one embodiment, the amphiphilic molecule is selected from the group consisting of phospholipids, phosphoglycerides, spingolipids, prostaglandins, saturated fatty acids, unsaturated fatty acids and soaps. In another embodiment, the amphiphilic molecules are commercially available, membrane-forming lipids that generally contain one polar headgroup and two non-polar alkyl sidechains, wherein at least one of the sidechains contains an ω-carboxyl functional group for covalent linkage to an amine modified silica surface (Regis Technologies, Morton Grove, Ill.). In a preferred embodiment, the commercially available amphiphilic molecules are membrane forming ligands, such as, phosphatidyl choline (PC), phosphatidylethanolamine (PE), phosphatidylglycerol (PG), phosphatidic acid (PA), and phosphatidylserine (PS) (see, e.g., Pidgeon et al., *Anal. Chem.* 66, 2701-2709 (1994)). In a more preferred embodiment, the amphiphilic molecules are those described in U.S. Pat. Nos. 4,927,879 and 4,931,498 and references incorporated therein. In a preferred embodiment, the amphiphilic molecule is a phospholipid. In another preferred embodiment, the amphiphilic molecule is phosphatidyl choline.

The composition comprises a mucin-type protein, mucin-type peptide or a combination thereof. The composition may comprise one or more types of mucin-type protein, mucin-type peptides, or combinations thereof. The mucin class of proteins consists of 13 proteins to date, of which ten are present in the gastrointestinal tract (Cornfield et al., *Front. Biosci.* 6, d1321-1357 (2001)). Mucins from different mucosal surfaces can be either membrane-bound or secreted. Mucins commonly feature tandem repeats (TR) of amino acid sequences that are largely comprised of serine, threonine, alanine, glycine, and proline (see, e.g., Table 1). MUC5AC and MUC6 are expressed largely in the epithelia of the stomach. MUC2 is expressed in both small and large intestine portions of the gastrointestinal tract. The mucin-type proteins may comprise all or a part of the amino acid sequence or carbohydrate components of a naturally-occurring mucin. In a preferred embodiment, the mucin-type protein comprises the entire amino acid sequence and carbohydrate components of a naturally-occurring mucin. In a preferred embodiment, the mucin-type peptides generally comprise only a part of a naturally-occurring mucin.

TABLE 1

Type and tandem repeat amino acid sequences in human mucins.

| Mucin | Chromosomal Location | Type* | Tandem Repeat | |
|---|---|---|---|---|
| MUC1 | 1q21 | MB | PDTRPAPGSTAPPAHGVTSA | (SEQ ID NO:1) |
| MUC2 | 11p15.5 | S | PTTTPPITTTTTVTPTPTPTGTQT | (SEQ ID NO:2) |
| MUC3 | 7q22 | MB | HSTPSFTSSITTTETTS | (SEQ ID NO:3) |
| MUC4 | 3q29 | MB | TSSASTGHATPLPVTD | (SEQ ID NO:4) |
| MUC5AC | 11p15.5 | S | TTSTTSAP | (SEQ ID NO:5) |
| MUC5B | 11p15.5 | S | SSTPGTAHTLTMLTTTATTPTATGSTATP | (SEQ ID NO: 6) |
| MUC6 | 11p15.5 | S | SPFSSTGPMTATSFQTTTTYPTPSHPQTTLPT HVPPFSTSLVTPSTGTVITPTHAQMATSASIH STPTGTIPPPTTLKATGSTHTAPPMTPTTSGY SQAHSSTSTAAKTSTSLHSHTSSTHHPEVTPT STTTITPNPTSTGTSTPVAHTTSATSSRLPTP FTTHSPPTGS | (SEQ ID NO: 7) |
| MUC7 | 4q13-q21 | S | TTAAPPTPSATTPAPPSSSAPG | (SEQ ID NO: 8) |

TABLE 1-continued

Type and tandem repeat amino acid sequences in human mucins.

| Mucin | Chromosomal Location | Type* | Tandem Repeat | |
|---|---|---|---|---|
| MUC8 | 12q24.3 | S | TSCPRPLQEGTPGSRAAHALSRRGHRVHELPT SSPGGDTGF | (SEQ ID NO: 9) |
| MUC9 | 1p13 | S | VGHQSVTPGEKTLTS | (SEQ ID NO: 10) |
| MUC11 | 7q22 | S | SGLSEESTTSHSSPGSTHTTLSPASTTT | (SEQ ID NO: 11) |
| MUC12 | 7q22 | MB | SGLSQESTTFHSSPGSTHTTLSPASTTT | (SEQ ID NO: 12) |

*MB = membrane-bound and S = secreted.

In a preferred embodiment, the composition comprises a mucin-type protein or mucin-type peptide derived from or the same as MUC2, MUC5AC, MUC5B, or MUC6. In a more preferred embodiment, the composition comprises MUC5AC or MUC2. In a more preferred embodiment the composition comprises MUC5AC.

In another aspect, the composition comprises a mucin-type protein or peptide having particular types of glycosylation. Mucin-type proteins or peptides may be O-linked glycosylated at threonine and serine residues found in the polypeptide chain. In one embodiment of this invention, the mucin-type protein or peptide contains threonine and serine amino acid residues that are fully O-linked glycosylated at all hydroxyl groups in the polypeptide, partially O-linked glycosylated, or non-glycosylated at the hydroxyl group of the amino acid side chain. In another embodiment of the invention, the mucin-type protein or peptide is between 50-80% O-linked glycosylated. The polypeptide may be glycosylated with monosaccharides, disaccharides, oligosaccharides, and polysaccharides. A preferred oligosaccharide is Gal β(1-3)-GalNAc α(1-O)—, Gal β(1-3)-[GlcNAc β(1-6)]-GalNAc α(1-O)—, GlcNAc (1-3)-GalNAc α(1-O)—, GlcNAc β(1-3)-[GlcNAc β(1-6)]-GalNAc α-(1-O)—, GalNAc α(1-3)-GalNAc α-(1-6)—, or Gal β(1-3)-[Gal β(1-6)]GalNAc α(1-O)—. In another embodiment, the disaccharide is Galβ(1-3) GalNAc α-. In another embodiment, the monosaccharide is GalNAc.

Similarly, mucin-type proteins or peptides may be N-linked glycosylated at asparagine amino acid residues found in the polypeptide chain. N-glycosylation may occur at asparagine residues wherein the asparagine is present in the sequence of amino acids Asn-X-Ser or Asn-X-Thr, wherein X is any amino acid other than proline and aspartic acid. Thus, another embodiment of the present invention, the mucin-type protein contains asparagine amino acid residues that are fully N-linked glycosylated at all side-chain amide nitrogens in the polypeptide, partially N-linked glycosylated, or non-glycosylated at the amide group of the amino acid side chain. The polypeptide may be glycosylated on asparagine residues with monosaccharides, disaccharides, oligosaccharides, or polysaccharides. Preferably, the side chain is N-linked glycosylated with a hexasaccharide, GlcNAc$_3$Man$_3$.

In another embodiment, the composition comprises a mucin-type peptide that is non-glycosylated. In another embodiment, the mucin-type peptide, whether glycosylated or not, is an epitope associated with mucin from either malignant or normal cells. In a preferred embodiment, the epitope is an amino acid sequence. In another preferred embodiment, the epitope is a sequence of sugar residues.

This invention also provides a composition wherein the mucin-type protein or mucin-type peptide is a secreted form or membrane-bound form of mucin. The mucin-type protein or mucin-type peptide may be derived from or is the same as a mucin derived from the GI tract, eye, trachea, lungs, salivary glands, sweat glands, breast, reproductive tract, pancreatic duct, gall bladder or urinary tract, e.g. the urethra and bladder. In a preferred embodiment, the mucin-type protein or mucin-type peptide is derived from or is the same as a mucin derived from the GI tract. In another embodiment, the mucin is derived from a normal or malignant cell, tissue or organ.

In a further embodiment, the present invention provides a mucin-type protein that is a mammalian mucin. The mammalian mucin may be derived from any species, including, without limitation, human, apes, monkey, rat, pig, dog, rabbit, cat, cow, horse, mouse, rat, and goat. In another embodiment, the present invention relates to a mucin-type protein or mucin-type peptide comprising one or more tandem repeat sequences selected from the group consisting of SEQ ID NOS:1-12.

The composition may further comprise other mucus layer components. Components of the mucus layer other than mucins include lipids, other non-mucin proteins, DNA, and carbohydrates. In another preferred embodiment, the composition further comprises non-mucin proteins. Non-mucin proteins that may interact with mucins include lysozyme, lactoferrin, immunoglobulins, protease inhibitors, growth factors, cytokines, defensins, β-galectins, trefoil factor peptides, IgG gamma Fc binding proteins, heparin and heparin sulfate, lipopolysaccharide binding proteins, and serum amyloid A proteins.

Examples of proteins specifically secreted in the gastrointestinal tract that interact with mucin include protease inhibitors such as, without limitation, 1-antitrypsin inhibitor, pancreatic secretory trypsin inhibitor (PSTI), and secretory leukocyte proteinase inhibitor; growth factors, which include mucosal integrity peptides (e.g., transforming growth factor-alpha and PSTI), luminal surveillance peptides (e.g., epidermal growth factors (EGF)), and rapid response peptides (e.g., trefoil factor family (TFF) peptides). The TFF peptides, sometimes referred to as P-domain peptides, include human spasmolytic peptide (TFF1), TFF2 and intestinal trefoil peptide (TFF3). Other proteins, such as alpha-defensins, HD5 and HD6, beta-defensin hBD1 and beta-galectins-1, 3 and 4 are also found in the gastrointestinal tract. See Cornfield et al., *Front. Biosci.* 6, d1321-1357 (2001).

The non-mucin proteins and mucin-type proteins and peptides may be isolated from a biological source or prepared by recombinant DNA methods, synthetic chemical routes, or a combination of any of these methods. Methods of preparing mucins from biological sources are well-known in the art. See Larhed et al., *J. Pharm. Sci.* 86, 660-665 (1997); Thorton et al., "Glycoprotein Methods and Protocols: The Mucins" in *Methods in Molecular Biology*, A. P. Corfield, Ed., Humana Press Inc., Totowa, N.J., 125, 77-85 (2000). Methods of preparing mucin-type proteins and mucin-type peptides recombinantly are known in the art. See Hu et al, *Cancer Research*, 53, 4920-4926 (1993); Dolby et al., *Protein Expression and Purification*, 15, 146-154 (1999). Preparation of peptides and proteins by chemical synthesis is known in the art. See *Solid-Phase Peptide Synthesis*, G. B. Fields, Ed., 1st ed., Academic Press, New York, 289 (1997); Fontenot et al., *Peptide Research*, 6, 330-336 (1993). In a preferred embodiment, the mucin-type protein is derived from a biological source. The mucin-type protein may be highly purified or may be a crude, relatively heterogeneous form. In a more preferred embodiment, the mucin-type protein is derived from pig.

Recombinant DNA methods include expressing the protein or peptide of interest from a host cell comprising a nucleic acid molecule, which in turn comprises a nucleic acid sequence encoding the protein or peptide of interest. The host cell may comprise a vector comprising the nucleic acid sequence. The vector may further comprise an expression control sequence operably linked to the nucleic acid sequence. In a preferred embodiment, the nucleic acid sequence encodes an amino acid sequence selected from the group consisting of a mucin-type protein and a mucin-type peptide. The mucin-type peptide may comprise a mucin epitope. The host cell may be a prokaryotic or a eukaryotic cell. In a preferred embodiment, the prokaryotic cell is an *E. coli* cell. In another preferred embodiment, the eukaryotic cell is selected from the group consisting of yeast, insect, and mammalian cells.

Methods for Preparing Chromatography Medium

Another aspect of the present invention is to provide a method for preparing a composition comprising a mucin-type protein or a mucin-type non-covalently immobilized to a solid support matrix, wherein said matrix is surface modified with an amphiphilic molecule. The method comprises the step of mixing a solution comprising a mucin-type protein and/or mucin-type peptide with a solid support matrix, wherein the matrix surface is modified with an amphiphilic molecule, under conditions in which the mucin-type protein, mucin-type peptide or combination thereof is adsorbed to the matrix. The mixture of mucin-type protein to mucin-type peptide can range from 1:99 parts mucin-type protein:peptide to 99:1 mucin-type peptide: protein.

In a preferred embodiment, the mucin-type protein or mucin-type peptide is a 10% (w/v) solution of mucin-type protein or peptide in a solvent. In another preferred embodiment, the solvent is polar. In a more preferred embodiment, the polar solvent is acetone or DPBS/Brij-35. In yet another preferred embodiment, the matrix is present in a ratio of 1:4 to 4:1 (w/v) to said 10% (w/v) solution of protein/peptide in a solvent. In a more preferred embodiment, the matrix is present in a ratio of about 2:1 (w/v) to said 10% (w/v) solution of protein/peptide in a solvent.

In another preferred embodiment of the present invention, the mixing step comprises stirring the mixture in a closed vial at a time and temperature sufficient to allow the mucin-type protein or mucin-type peptide to equilibrate with the solid support matrix. In one embodiment, the equilibrium takes about 1-2 hrs at a temperature up to 25° C. In yet another preferred embodiment, the method comprises the steps of washing, drying or subsequently washing and drying the mixture. In a more preferred embodiment, the drying step comprises evaporating said solvent in air or by rotoevaporation. In yet another preferred embodiment, the dried mixture is packed in a column for use in liquid chromatography, high performance liquid chromatography, or fast performance liquid chromatography; coating a glass slide for thin layer chromatography; or coating a multi-well plate for HTS.

The method may optionally comprise adsorbing other molecules from the mucus layer, including other proteins, DNA, RNA, lipids or carbohydrates. Other molecules may be immobilized using methods known in the art. See, e.g., Zhang et al. in which nicotinic acetylcholine receptors (nAChR) were immobilized to IAM HPLC supports (*Anal. Biochem.* 264, 22-25 (1998)) and Chui et al., in which enzymes such as α-chymotrypsin and trypsin were immobilized to IAM supports (*Anal. Biochem.* 201, 237-245 (1992)). Macromolecular structures such as rat liver microsomes have also been immobilized to IAM supports (Alebić-Kolbah and Wainer, *J. Chromatography* 646, 289-295 (1993)).

In one embodiment of the invention, a mucin-type protein is bound to a phosphatidylcholine carrier. In a preferred embodiment, porcine MUC5AC is used. In a more preferred embodiment MUC5AC is immobilized to IAM carrier particles (MUC5AC-IAM) at weight ratios of 10:1, 4:1, 2:1, 1:1, 1:2, 1:4, and 1:10. In an even more preferred embodiment of the present invention, a 2:1 ratio of MUC5AC to IAM particles is used. In another embodiment, chromatography columns are packed with immobilized MUC5AC-IAM particles having ratios of 1:4, 1:2, 1:1, and 2:1 (MUC5AC to IAM).

Methods for Determining In Vitro Drug Permeability Using MIC Media

For oral drug administration, bioavailability can be calculated by the following equation:

$$F = fa(1-E_G)(1-E_H), \quad [1]$$

where F is the bioavailability of a compound, fa is the extent of absorption in the intestinal mucosa, $E_G$ is the cytosolic localized metabolism in the enterocyte and $E_H$ is the extraction in the liver including both metabolism and biliary secretion (Lennernäs, H., "Human Perfusion Studies" in *Oral Drug Absorption: Prediction and Assessment*, Dressman, J. and Lennernäs, H., Eds., 106, 99-117 (2000)). The effective permeability of a drug may be used to estimate fa. Thus, determining the effective permeability is an important part of estimating bioavailability.

Effective permeability is estimated from the thickness of the mucin-type protein or mucin-type peptide layer non-covalently immobilized to the solid support matrix, the membrane diffusion coefficient of the drug, and the membrane equilibrium coefficient for the mucin-type protein or mucin-type peptide layer non-covalently immobilized to the solid support matrix. The membrane equilibrium coefficient is determined from the volume of the mobile phase, the interstitial volume of the stationary phase, and the partition ratio, which is further determined from the retention time of the drug candidate and the void volume of the column, as discussed below.

The effective permeation of a drug through a membrane is given by the equation, $$P_{\mathit{eff}} = \frac{D_m K_m}{L}, \quad [2]$$

where $D_m$ is the membrane diffusion coefficient of the solute, $K_m$ is the membrane equilibrium constant, and L is the membrane thickness (Stein, W., *Transport and Diffusion Across Cell Membranes*, Academic Press, Orlando, Fla. (1986)). $D_m$ depends on the molecular size of the drug and is proportional to the inverse of molar volume of the drug (Pidgeon and Ong, *Chemtech*. June, 38-48 (1995); Xian and Anderson, *Biophys. J.*, 66, 561-573 (1994)). Since molecular weight, MW, is proportional to molecular size, $D_m$ may also written as, $$D_m = \frac{1}{MW}. \qquad [3]$$

Thus, $D_m$ can be calculated from the molecular weight. Furthermore, $K_m$ is calculated by the following equation, $$K_m = (V_m/V_s)k', \qquad [4]$$

where $V_m$ is the volume of the mobile phase, $V_s$ is the internal volume of the stationary phase, and k' is the partition ratio (Pidgeon and Ong, *Chemtech*. June, 38-48 (1995)). The partition ratio is determined by the equation, $$k' = (t_r - t_o)/t_o, \qquad [5]$$

where $t_r$ is the retention time of the drug and $t_o$ is the void volume of the column. Both $t_r$ and $t_o$ can be experimentally determined in order to obtain k'.

The thickness of the mucin layer, L, may be determined by any method known in the art. In a preferred embodiment, the mucin-layer thickness is determined by confocal microscopy. According to this invention, all values of L measured by this method are determined by averaging the thickness of the mucin layer on each of 10-15 beads. The use of the term "about" in connection with defining thickness (L) refers to a value that is similar to the defined thickness. For example, an L value of "about" a particular defined thickness would be a thickness within 10%, preferably 5%, more preferably 2%, of the defined thickness. Furthermore, detection of the layer thickness by confocal microscopy can be accomplished using a mucin-specific antibody. In a more preferred embodiment, the antibody may be an anti-MUC5AC antibody labeled with biotin and streptavidin labeled with Alexa Fluor 488.

Equation 2 can be used to determine $K_m$ for a given MIC medium. Both $D_m$ and L are known from the discussion above, and $P_{eff}$ can be calculated for various drugs having known in vivo absorption. For example, a number of drug permeability coefficients, $P_{eff}$, derived from in vivo experiments are listed in literature. Plotting various known drug permeability coefficients as a function of the measured k' values for the same drugs on a separation media will result in a correlation equation that can be used to determine other $P_{eff}$ values not found in literature. See Example 5 below. Once $K_m$ has been calculated in this manner for a specific MIC medium, compounds having unknown $P_{eff}$ can be determined.

Methods for Estimating Drug Permeability

The MIC media may be used in any method, including, inter alia, batch chromatography or column chromatography. Column chromatography includes liquid chromatography, high performance liquid chromatography, and fast performance liquid chromatography. The MIC media may also be used to coat a slide or plate for thin layer chromatography. In another embodiment, the MIC media may be used to coat a multi-well plate for HTS or other high-throughput analyses. The MIC media may be used to separate components in a mixture from one another using methods well-known in the art.

Another aspect of the present invention is to provide an in vitro method for estimating drug absorption through the mucus layer. This method comprises determining an effective permeability coefficient ($P_{eff}$) for a drug compound using MIC media.

In one aspect, the invention provides a method of estimating the permeability coefficient of one or more drugs by contacting the drug with the MIC media, measuring the degree of binding of the drug on the MIC media and estimating the drug permeability coefficient. In a preferred embodiment, the contacting step is performed by loading the drug on a column comprising the MIC media and the measuring step is performed by measuring the retention time of the drug on the column. In one embodiment, the drug permeability coefficient is estimated for a single drug.

In another preferred embodiment, permeability coefficients of a number of drugs are measured either sequentially, by contacting each drug with the MIC media one by one and measuring binding of the drug to the media, or simultaneously, by contacting a mixture of more than one drug with the MIC media and measuring binding of the drug to the media. In another embodiment, the MIC media comprises types and/or amounts of mucin-type protein or mucin-type peptide to mimic the mucus layer in a specific cell, tissue or organ. These include the mucus layer of the GI tract, eye, trachea, lungs, salivary glands, sweat glands, breast, reproductive tract, pancreatic duct, gall bladder or urinary tract.

In another aspect, the method may be used to compare the relative permeability of one or more drugs to each other or to drugs having a known permeability. The method comprises contacting the MIC media with a drug of interest and measuring the degree of binding of the drug to the MIC media, then comparing the degree of binding to that measured for one or more other drugs. The other drug may be one having an unknown drug permeability coefficient or may be one having a known drug permeability coefficient. The method may be used to determine whether the drug of interest has a greater or lesser relative permeability compared to the other drug. Further, by comparing the drug of interest to one or more other drugs having a known permeability coefficient, one may estimate the permeability coefficient for the drug of interest. The degree of binding may be measured sequentially or simultaneously. The degree of binding may be determined using column chromatography or by batch chromatography. See Example 5.

Another embodiment of the invention is to provide a method for estimating effective permeability coefficients of one or more drugs in two or more physiological states by changing the amount and/or type of mucin-type protein or mucin-type peptide in the MIC media. In one preferred embodiment, the MIC media comprises types and/or amounts of mucin-type proteins or mucin-type peptides that mimic the mucus layer in a healthy state or in a diseased states. In another embodiment, the method provides a method for estimating effective permeability coefficients of one or more drugs in two or more physiological states by changing the mobile phase of the media. In a preferred embodiment, the pH, osmolarity and/or surfactant concentration or type is altered to mimic a particular physiological state.

The MIC media may be used to mimic the healthy or diseased state of any mucosal layer, including the gastrointestinal tract, reproductive tract, urinary tract, eye, mouth, salivary glands, pancreatic glands, sweat glands or gall bladder. In a preferred embodiment, the diseased state is an epithelial cell cancer. The types and amounts of mucin-type proteins and mucin-type peptides representative of healthy states and disease states of the intestine can be determined by one having ordinary skill in art (Cornfield et al., *Frontiers in Bioscience*, 6, d1321-1357 (2001); Bhavanadan, V. P., *Glycobiology*, 1, 493-503 (1991); Zotter et al., *Cancer Rev.*, 11-12, 55-101, (1988); Fink, M. P., *Crit. Care Med.*, 19(5), 627-641 (1991)).

In another embodiment, the different physiological states are different developmental stages, e.g., infant, child, adolescent and adult. In another embodiment, the different physiological states may be mucosal layers from different cells, tissues, or organs. For example, one may compare estimated drug absorption in the mouth, gastrointestinal tract and reproductive tract to determine the best method of administration.

A further embodiment of this invention is to provide a method for emulating an absorption process in a system comprising more than one epithelial mucosal layer. The method comprises estimating drug permeability coefficients using a series of chromatography columns each having a different amount and/or type of a mucin-type protein, mucin-type peptide, or combination thereof immobilized to a chromatography medium, wherein the different amounts and/or types of mucin-type proteins or mucin-type peptides mimic the different mucus linings in the system. In a preferred embodiment, the mobile phase may be altered to mimic the different extracellular fluids in the system. In a preferred embodiment, the system is the digestive system. For example, the thickness of the mucus lining along the gastrointestinal tract varies according to the cellular and glandular tissues associated with the location. The thickness of the mucus layer in the esophagus has been measured to be between 83-107 μm, the stomach between 92-196 μm, the duodenum between 11-21 μm, the proximal colon between 59-155 μm, the sigmoid colon between 19-113 μm, the distal colon between 66-202 μm, and the rectum between 101-209 μm (see, e.g., Corfield et al., *Frontiers in Bioscience* 6, 1321-1357 (2001) and references therein).

In a preferred embodiment, the invention provides column chromatography wherein the stationary phase comprises MUC5AC-IAM and the mobile phase comprises an aqueous buffer solution employed at conditions matching those of the GI tract. For instance, to simulate gastrointestinal conditions, sample sets may be analyzed using a mobile phase of between pH 2 and pH 8 using MIC media. Other variables such as osmolarity, surfactant concentration, lipid concentration, digestive enzyme concentration, bile acid concentration, and other GI components may also be added to the mobile phase to match conditions representative of the GI tract.

Another embodiment of the present invention is a kit comprising the MIC media. The kits may be used to estimate absorption of one or more drugs. In one embodiment, diagnostic kits can include but are not limited to one or more standards, such as a drug having a known in vivo drug permeability coefficient and one or more MIC media.

Another embodiment of the present invention comprises a method for using MIC in HTS. In a preferred embodiment, HTS includes HPLC or ELISA.

EXAMPLES

The following materials were used in the examples set forth below.

Materials

Type II mucin, crude from porcine stomach, was obtained from Sigma Chemicals (St. Louis, Mo.), polyethylene glycol dodecyl ether (Brij-35 P) was purchased from Fluka Chimica, benzyl alcohol was purchased from Fisher (Pittsburgh, Pa.), acetone was obtained from Fisher, and Dulbecco's phosphate buffered saline (DPBS) was obtained from JRH Biosciences (Lenexa, Kans.). Model drug compounds differing in their physiochemical properties and listed in Table 3 were purchased from Sigma Chemicals (St. Louis, Mo.). Mucin (MUC-5AC) antibody was obtained from NeoMarkers, Lab Vision Corporation (Fremont, Calif.) and biotin-XX goat anti-mouse IgG (H+L) and streptavidin linked to Alexa Fluor 488 were purchased from Molecular Probes (Eugene, Oreg.). Immobilized artificial membrane columns and loose packing material containing silica modified with diacylated phosphatidyl choline ligands and endcapped with C10/C3 alkyl chains (IAM.PC.DD2 and loose IAM.PC.DD2, 10×4.6 mm, 12 μm, 300 Å) were purchased from Regis Technologies (Morton Grove, Ill.). Dialysis tubing having a molecular weight cutoff (MWCO) of 8,000 was purchased from Spectrum Laboratories (Houston, Tex.). BCA Protein assay kits were obtained from Pierce Endogen (Rockford, Ill.).

Example 1

Non-Covalent Immobilization of Mucin to IAM Phosphatidylcholine Material

In order to investigate the adsorption of mucin to the column packing material, the ratio of mucin to IAM.PC.DD2 was varied. Aliquots of 20 mg of IAM.PC.DD2 were with varying amounts of 10% (w/v) mucin in either acetone or mobile phase solution (MPS) [DPBS (0.05M), Brij-35 (0.02 M), and benzyl alcohol (1% v/v) at pH 7 or pH 3] to give ratios of 10:1, 4:1, 2:1, 1:1, 1:2, 1:4, and 1:10 (w/w) of IAM.PC.DD2 to mucin. Each mixture was incubated at room temperature (rt) for 1 hour (h) with constant mixing prior to being washed 5 times with MPS. After each wash, the samples were sedimented by centrifugation (at 3000 g for 10 sec) and the supernatants were monitored for protein content by BCA assay according to manufacturer's instructions. Solutions containing a known quantity of mucin were used to generate standard curves for the BCA assays. The amount of the mucin absorbed to IAM.PC.DD2 was quantified. Without being bound by theory, applicants believe that the nature of the non-covalent interaction between mucin and IAM.PC.DD2 is electrostatic.

Large scale preparation of packing material for MIC columns was performed by mixing 300 mg of IAM.PC.DD2 with 10% (w/v) mucin in acetone to yield 4:1, 2:1, 1:1, 1:2, and 1:4 (w/w) ratio of IAM.PC.DD2 to mucin. The mixtures were stirred in closed vials for 1 h at room temperature before being dried. Four columns (10×4.6 mm) having mucin to IAM-PC ratios of 1:4, 1:2, 1:1, 2:1 were prepared by Regis Technologies using this material. Table 2 and FIG. 1 illustrate an optimization plot between the amount of mucin absorbed to IAM beads versus the weight ratio of mucin to IAM beads.

TABLE 2

Binding optimization results Between mucin and IAM beads.

| Initial Ratio (mucin:IAM) | Mucin Absorbed to IAM Beads (mg) | Final Ratio (mucin:IAM) |
|---|---|---|
| 10:1 | 6.51 | 1.34 |
| 4:1 | 7.40 | 1.46 |
| 2:1 | 7.22 | 1.46 |
| 1:1 | 2.50 | 0.47 |
| 1:2 | 1.21 | 0.24 |
| 1:4 | 0.81 | 0.16 |
| 1:10 | 0.05 | 0.01 |

Example 2

Analysis of Immobilized Mucin on Phosphatidylcholine Carrier (PC) with Transmission Electron Microscopy (TEM)

PC carriers with and without immobilized mucin were fixed with a ruthenium-osmium mixture using the modified protocol of Luft (*Anal. Rec.* 171, 369-416 (1977)). Carriers were then sectioned to a thickness of 120-200 nm. Sample sections were contrasted with uranyl acetate and lead citrate and were fixed on carbon-stabilized, formvar-coated, 50 mesh, copper grids. A Hitachi 7110 Scanning Transmission Electron Microscope was used to acquire images.

Figure 2A:
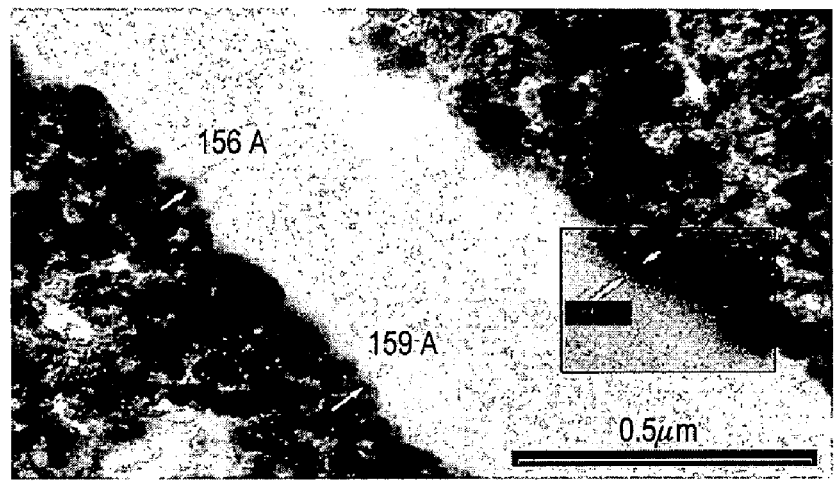
FIGS. 2(a) and 2(b) show a transmission electron micrograph (TEM) of MUC-5AC to IAM particles
Figure 2B:
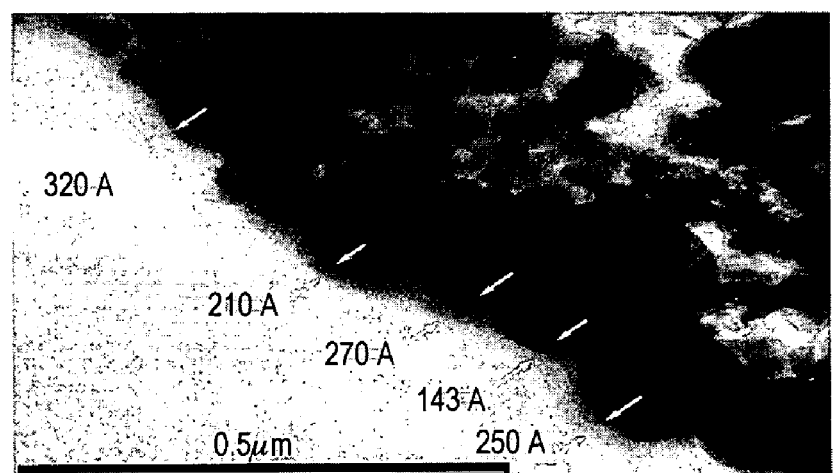
Figure 2C:
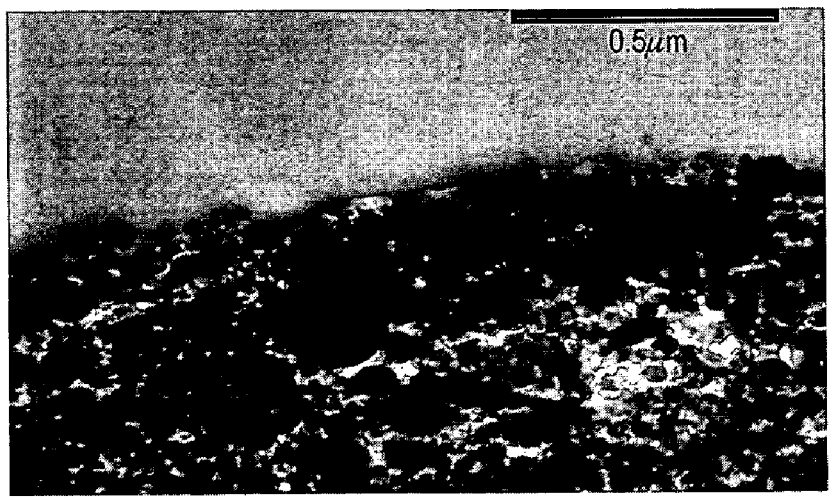
FIG. 2(c) shows a TEM of IAM beads without mucin. See Example 2.

FIGS. 2(*a*) and 2(*b*) illustrate the immobilization of MUC-5AC to the IAM particles as confirmed by TEM analyses. The Luft's fixation-staining technique (Luft, *Anal. Rec.* 171, 369-416 (1977)) provided low electron contrast for visualization of mucopolysaccharides. The images revealed that MIC particle surfaces appear to have a hazy, ill-defined edge which was opposite of the sharp edge found in non-immobilized IAM beads (FIG. 2(*c*)). The observed electron dense surface coatings ranged from 14 nm to 38 nm for the MUC5AC-IAM particles.

Example 3

Detection of Mucin Membrane Thickness with Confocal Microscopy

Mouse monoclonal antibodies (1 µg/ml) having cross-reactivity to MUC5AC were immobilized to surfaces of MIC beads having ratios of 0:1, 1:4, 1:1 and 4:1 mucin to IAM beads by incubation at rt for 1 hr with constant vortexing. The beads were washed five times with DPBS. Biotin labeled goat anti-mouse antibodies (1 µg/ml) were then reacted with these beads at rt for 1 h with constant mixing. The beads were then washed five times with DPBS. Streptavidin labeled with Alexa Fluor 488 (5 µg/ml) was then added to the coated beads. The beads were washed before being analyzed by confocal microscopy using a Biorad Radiance 2000 MP confocal imaging system attached to an Olympus BX50WI upright microscope. The thickness of the absorptive layer was calculated using an intensitometric approach (Leung and Jeun, *Microscopical Society of Canada Bulletin*, 20, 26-33 (1992)).

Figure 3A:
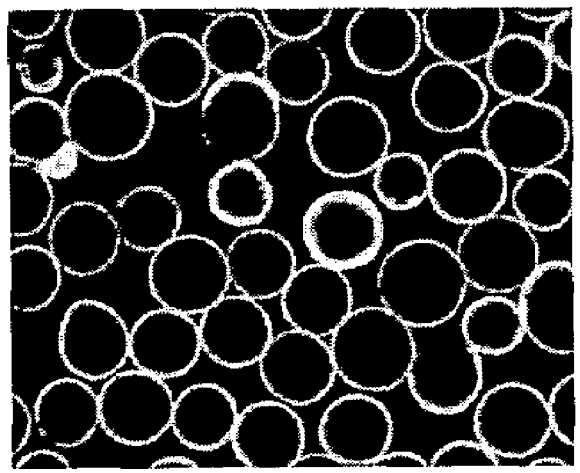
FIGS. 3(a) and 3(b) show confocal micrographs and FIG. 3(c) show a phase contrast micrograph of MUC5AC-IAM particles. Anti-MUC5AC antibody was labeled with biotin and visualized with streptavidin labeled with Alexa Fluor 488. See Example 3.
Figure 3B:
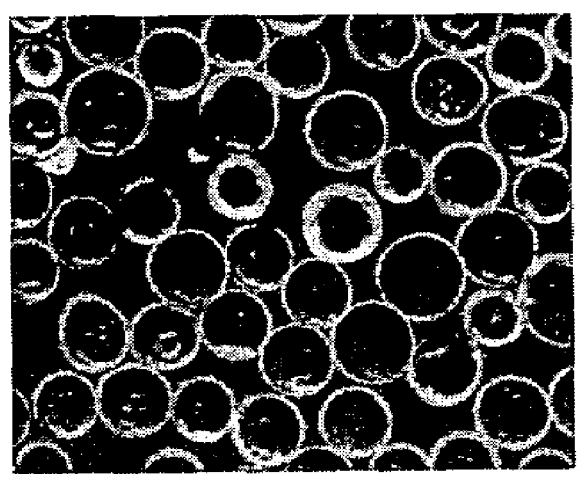
Figure 3C:
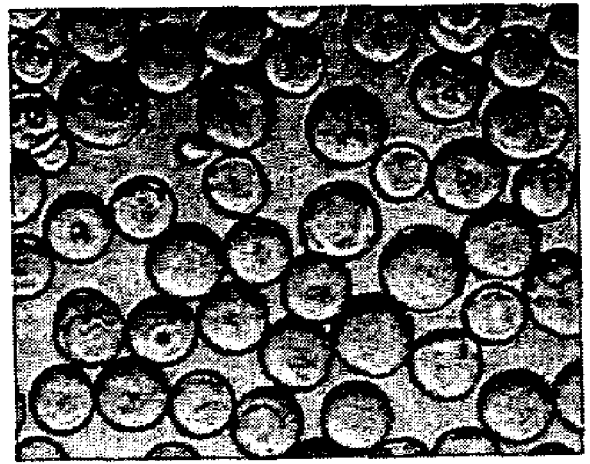

Mucin thickness was determined by averaging 10-15 measured thicknesses for each ratio of mucin to IAM beads used. FIG. 3 shows a cross-section of MUC5AC-IAM beads where the mucin layer is visualized by staining as indicated by the rings present. Due to the variability in sectioning, some of the beads appeared to have thicker rings than others. In a preferred embodiment, confocal measurements for a series of ratios of mucin to loose PC particles (1:4, 1:1, and 4:1) were determined. The thickness increased from 0.3 µm, the thickness of a bare phospholipid layer on a silicon carrier, to 0.38 µm, the thickness corresponding to the 4:1 ratio of mucin to IAM particles beads. Without being bound by theory, applicants believe that the mucin partially intercalates the phospholipid layer. Additionally, the thickness of mucin:IAM beads having ratios of 1:4 and 1:1 were 0.326 and 0.35 µm, respectively. A plot of mucin:IAM ratio to measured thickness was approximately linear as shown in FIG. 4 and could be used to extrapolate other mucin:IAM bead ratios such as 2:1 (0.36 µm). Membrane thickness, L, was then used to calculate $K_m$ as discussed above.

Example 4

Determination of Mucin and Drug Interaction

A known amount of a drug compound or an enzyme was dissolved in 10% (w/v) mucin in mobile phase solution. The sample was incubated for 1 h with constant mixing at rt before being transferred to dialysis tubing having a MWCO of 8000. The sample was then dialyzed against deionized (DI) water overnight at rt before further dialysis with fresh DI water for another 12 h at rt. The dialyzed media were analyzed by reversed phase HPLC to determine the amount of drug released to the environment. The percent of drug immobilized to mucin was determined by subtracting the amount of drug released into dialysis medium from the amount of drug mixed with the mucin.

Example 5

Estimation of Drug Absorption by High Performance Liquid Chromatography (HPLC)

Columns containing 1:4, 1:2, 1:1, and 2:1 wt % of mucin to PC IAM particles were packed and used to determine drug retention times. It was observed that the column containing the 1:4 ratio provided the longest drug retention times. Without being bound by theory, applicants believe that these results are related to the physiochemical properties, specifically hydrophobicity, of mucin itself. For example, the immobilization of mucin most likely involves the non-covalent entrapment of hydrophobic groups from the mucin molecule with the hydrophobic pockets of the IAM molecules attached to silica. With an increase of mucin to IAM beads, the chromatography medium becomes more hydrophobic because there are more hydrophobic groups from mucin available to interact with a limited number of hydrophobic groups within the IAM beads. The smaller 1:4 ratio of mucin to IAM beads results in a similar number of hydrophobic interactions between mucin and IAM. This would then allow the hydrophilic groups of the mucin to be available for binding drug candidates and would result in increased retention times of hydrophilic drugs on the mucin to IAM chromatography medium. For subsequent experiments, a 2:1 column was used to determine drug retention times and calculate $k'_{MIC}$ (see equations 1-5 and Table 4 below).

The bioavailability of twenty-nine different compounds were used for comparing in vitro and in vivo models (see Table 3). The in vivo bioavailability values for single-pass perfusion permeability coefficient (Loc-I-Gut) and in vitro parameters for IAM and Caco-2 models were obtained from the literature. See Table 3.

TABLE 3

| | Known Bioavailability Values for Pharmaceutical Compounds. | | |
|---|---|---|---|
| N | Bioavailability (% Absorbed) | Compound | Reference |
| 1 | 80 | acetaminophen | NA |
| 2 | 68 | acetyl salicylic acid | 1 |
| 2 | 100 | acetyl salicylic acid | 2 |

TABLE 3-continued

Known Bioavailability Values for Pharmaceutical Compounds.

| N | Bioavailability (% Absorbed) | Compound | Reference |
|---|---|---|---|
| 3 | 20 | Acyclovir | 2 |
| 3 | 30 | Acyclovir | 1 |
| 4 | 0 | α-methyldopa | 3 |
| 5 | 93 | Alprenolol | 2 |
| 6 | 100 | Antipyrine | 3, 4 |
| 7 | 50 | Atenolol | 3, 4 |
| 8 | 100 | Caffeine | 5 |
| 9 | N/A | carbamazepine | NA |
| 10 | 62 | Cimetidine | 1 |
| 10 | 95 | Cimetidine | 2 |
| 11 | 100 | corticosterone | 2 |
| 12 | 0 | Creatine | 3, 6 |
| 13 | 60 | enalapril maleate | 3, 6 |
| 13 | 100 | enalapril maleate | 7 |
| 14 | 60 | Furosemide | 3, 4 |
| 15 | 100 | Ibuprofen | 1 |
| 16 | 100 | Ketoprofen | 4 |
| 17 | 90 | Labetalol | 2 |
| 18 | 16 | Mannitol | 2 |
| 18 | 17 | Mannitol | 8 |
| 19 | 95 | Metoprolol | 2 |
| 20 | 100 | Naproxen | 4, 8 |
| 21 | 10 | PEG 900 | 1, 8 |
| 22 | 0 | PEG 4000 | 8, 9 |
| 22 | 10 | PEG 4000 | 1 |
| 23 | 90 | Propranolol | 2 |
| 23 | 100 | Propranolol | 3, 6 |
| 24 | 80 | quinidine, HCl | 1 |
| 25 | 13 | sulfasalazine | 2 |
| 26 | 60 | Terbutaline | 2, 4, 7 |
| 26 | 73 | Terbutaline | 2, 4, 7 |
| 27 | 72 | Timolol | 2 |
| 28 | 60 | Verapamil | 3 |
| 29 | 98 | Warfarin | 2 |

[1] Yee, S., Pharm. Res. 14 (6), 763-766 (1997).
[2] Yazdanian et al., Pharm. Res. 15 (9), 1490-1494 (1998).
[3] Winiwarter et al., J. Med. Chem. 41, 4939-4949 (1998).
[4] Fagerholm et al., Pharm. Res. 13 (9), 1336-1342 (1996).
[5] Levin, J. Med. Chem. 23, 682-684 (1990)
[6] Lennernäs et al., Pharm. Res. 14 (5), 667-671 (1997).
[7] Fagerholm et al., J. of Drug Targeting 3, 191-200 (1995).
[8] Rubas et al., Pharm. Res. 10, 113-118 (1993).
[9] Sandstrom et al., Br. J. Clin. Pharmacol. 48, 180-189 (1999).

Chromatograms were acquired on a Thermo Separations HPLC instrument (San Jose, Calif.) equipped with 10×4.6 mm IAM.PC.DD2, Discovery C18 column, or MIC columns. Samples were dissolved in mobile phase solution and filtered (filter pore size, 0.45 μm) prior to injection. Elution profiles were monitored in the UV-Vis range using an isocratic method (0.3 ml/min at either 37.4° C. or 30° C. using MPS at pH 7.4). The 29 samples provided in Table 3 were loaded on the column and their retention times were measured. From this measurement and a measurement of the void volume ($t_0$) the $k'_{MIC}$ could be determined. In addition, from the molecular weight of the compounds, $D_m$ could be determined. $P_{eff}$ was known for the compounds listed in Table 5. These compounds, with the exceptions noted below, were used to generate the column constant ($V_m/V_s$). See FIG. 5.

Figure 5:
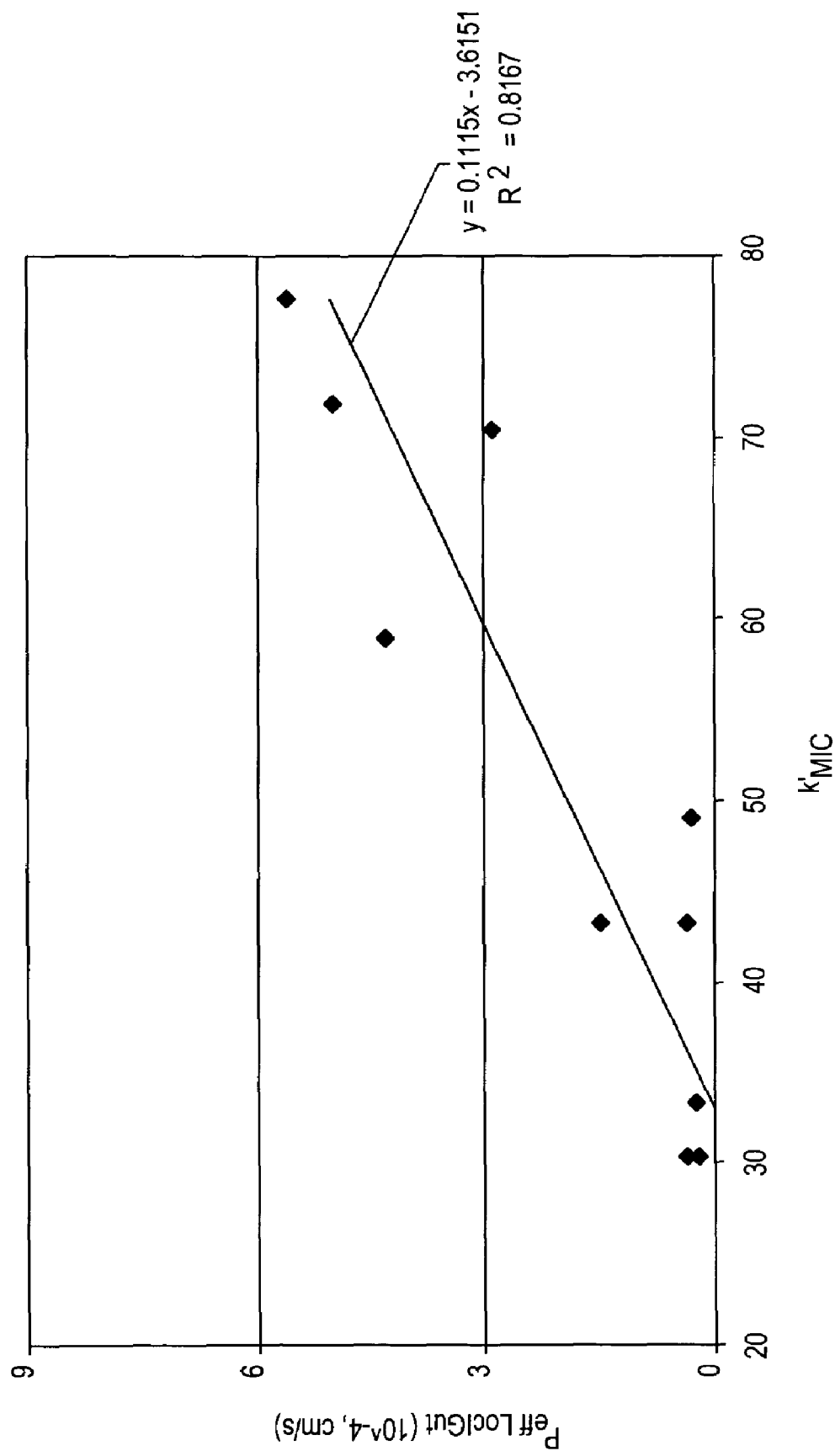
FIG. 5 illustrates the correlation between $P_{\it{eff\,Loc\text{-}I\text{-}Gut}}$ and $k'_{MIC}$. See Example 5.

FIG. 5 shows the correlation between effective permeability, $P_{effLoc-I-Gut}$, and capacity factor, $k'_{MIC}$. Since MIC is valid for passive diffusion transport, any data corresponding to carrier mediated transport, such as α-methyldopa and creatine, were not included in the plot. In addition, enalapril maleate was reported to have a percent absorption value of either 60 or 100 (Winiwarter et al., J. Med. Chem. 41, 4939-4949 (1998); Lennernäs et al., Pharm. Res. 14 (5), 667-671 (1997); Fagerholm et al., J. of Drug Targeting 3, 191-200 (1995)). During the HPLC analyses, it appears that enalapril maleate was hydrolyzed to enalaprilat, as confirmed by the presence of two peaks corresponding to the hydrolyzed and non-hydrolyzed forms (http://www.rxlist.com/cgi/generic/enalap.htm). The value corresponding to the hydrolyzed form was used to generate FIG. 5. In addition, values corresponding to $P_{effLoc-I-Gut}$ and $k'_{MIC}$ for both ketoprofen and naproxen were excluded. The correlation between mean data of $P_{effLoc-I-Gut}$ and $k'_{MIC}$ was best fit to an exponential curve, $y=0.0081e^{0.00634x}$. However, the linear fit, $y=0.1115x-3.6151$ ($R^2=0.8167$), was subsequently used to calculate the values of $P_{effMIC}$. See Table 4.

TABLE 4

HPLC Drug Permeability Values for Pharmaceutical Compounds Using MIC Media.

| Compound | Retention Time | $k'_{MIC}$ | Molecular Weight | $D_m$ | $K_m$ (×10$^{-6}$) | $P_{effMIC}$ |
|---|---|---|---|---|---|---|
| acetaminophen | 2.8 | 38.2857 | 151 | 0.0066 | 0.3559 | 0.6538 |
| Acetyl salicylic acid | 2.8 | 38.5714 | 180 | 0.0055 | 0.4477 | 0.6856 |
| Acyclovir | 2.4 | 33.5714 | 225 | 0.0044 | 0.1039 | 0.1281 |
| α-methyldopa | 2.4 | 33.2857 | 211 | 0.0047 | 0.0319 | 0.0963 |
| Alprenolol | 3.3 | 46.1429 | 286 | 0.0035 | 1.5740 | 1.5298 |
| Antipyrine | 5.5 | 77.5714 | 188 | 0.0053 | 3.4107 | 5.0341 |
| Atenolol | 2.2 | 30.4286 | 266 | 0.0038 | −0.2131* | −0.2223* |
| Caffeine | 2.7 | 37.5714 | 194 | 0.0051 | 0.4014 | 0.5741 |
| carbamazepine | 4.2 | 59.0000 | 236 | 0.0042 | 2.5209 | 2.9634 |
| cimetidine[1] | 2.4 | 33.2857 | 252 | 0.0039 | 0.0874 | 0.0963 |
| cimetidine[2] | 8.5 | 120.429 | 252 | 0.0040 | 8.9021 | 9.8127 |
| corticosterone | 4.3 | 60.4286 | 347 | 0.0029 | 3.8952 | 3.1227 |
| Creatine | 2.2 | 30.4286 | 113 | 0.0088 | −0.0905* | −0.2223* |
| Enalapril maleate[3] | 7.8 | 110.429 | 493 | 0.0020 | 15.4210 | 8.6977 |

TABLE 4-continued

HPLC Drug Permeability Values for
Pharmaceutical Compounds Using MIC Media.

| Compound | Retention Time | k'$_{MIC}$ | Molecular Weight | D$_m$ | K$_m$ (×10$^{-6}$) | P$_{eff\,MIC}$ |
|---|---|---|---|---|---|---|
| enalapril maleate[4] | 2.6 | 35.8571 | 493 | 0.0020 | 0.6790 | 0.3830 |
| furosemide | 3.5 | 49.0000 | 331 | 0.0030 | 2.2006 | 1.8484 |
| ibuprofen | 3.8 | 53.2857 | 228 | 0.0044 | 1.9119 | 2.3263 |
| ketoprofen | 3.8 | 52.5714 | 254 | 0.0039 | 2.0567 | 2.2466 |
| labetalol | 3.8 | 53.2857 | 365 | 0.0027 | 3.0559 | 2.3263 |
| mannitol | 2.4 | 33.4286 | 182 | 0.0055 | 0.0736 | 0.1122 |
| metoprolol | 3.1 | 43.2857 | 685 | 0.0015 | 2.9861 | 1.2113 |
| naproxen | 3.6 | 50.4286 | 230 | 0.0043 | 1.6642 | 2.0077 |
| PEG 900 | 2.4 | 33.2857 | 900 | 0.0011 | 0.3119 | 0.0963 |
| PEG 4000 | 2.4 | 33.2857 | 4000 | 0.0003 | 1.3861 | 0.0963 |
| propranolol | 5.0 | 70.4286 | 296 | 0.0034 | 4.5157 | 4.2377 |
| quinidine, HCl | 5.0 | 70.4286 | 379 | 0.0026 | 5.7804 | 4.2377 |
| sulfasalazine | 5.1 | 71.8571 | 398 | 0.0025 | 6.3063 | 4.3970 |
| terbutaline | 3.1 | 43.2857 | 274 | 0.0036 | 1.1961 | 1.2113 |
| timolol | 2.6 | 36.1429 | 433 | 0.0023 | 0.6459 | 0.4148 |
| verapamil | 5.1 | 71.8571 | 491 | 0.0020 | 7.7737 | 4.3970 |
| warfarin | 3.9 | 54.7143 | 308 | 0.0032 | 2.7587 | 2.4855 |

[1]Bioavailability = 62%;
[2]Bioavailability = 95%;
[3]Bioavailability = 100%;
[4]Bioavailability = 60%;
*negative values indicate that the compound is highly soluble in solvent.

TABLE 5

Effective permeability and capacity factors
for pharmaceutical compounds passively absorbed.

| % Absorbed | Drug | P$_{eff\,Loc-I-Gut}$ (×10$^{-4}$ cm/s)* | P$_{eff\,Loc-I-Gut}$ σ | K'$_{MIC}$ | P$_{eff\,MIC}$ (×10$^{-4}$ cm/s)** | P$_{eff\,Caco-2}$ (×10$^{-6}$ cm/s)*** |
|---|---|---|---|---|---|---|
| 100 | antipyrine | 5.6 | 1.6 | 77.57 | 5.03 | NA |
| 100, 90 | propranolol | 2.9 | 2.2 | 70.43 | 4.24 | 21.8 |
| 100 | naproxen | 8.0 | 4.2 | 50.43 | 2.01 | 74.2 |
| 100 | ketoprofen | 8.5 | 3.9 | 52 | 2.25 | NA |
| 95 | metoprolol | 1.5 | 0.9 | 43 | 1.21 | 23.7 |
| 60 | terbutaline | 0.3 | 0.3 | 43 | 1.21 | 0.47 |
| 60 | furosemide | 0.3 | 0.3 | 49.00 | 1.85 | NA |
| 60 | verapamil | 5.0 | 2.5 | 71.86 | 4.40 | NA |
| 60 | enalapril maleate | 0.2 | 0.3 | 35.86 | 0.38 | NA |
| 50 | atenolol | 0.15 | 2.0 | 30.43 | −0.22 | 0.53 |
| 0 | PEG 4000 | 0 | 0 | 33.29 | 0.10 | 0.97 |
| 0 | a- | 0.2 | 0.06 | 33.29 | 0.10 | NA |
| 0 | creatine | 0.3 | 0.2 | 30.43 | −0.22 | NA |
|   | carbamazepi | 4.3 | 2.7 | 59.00 | 2.96 | 19.9 |

Figure 6:
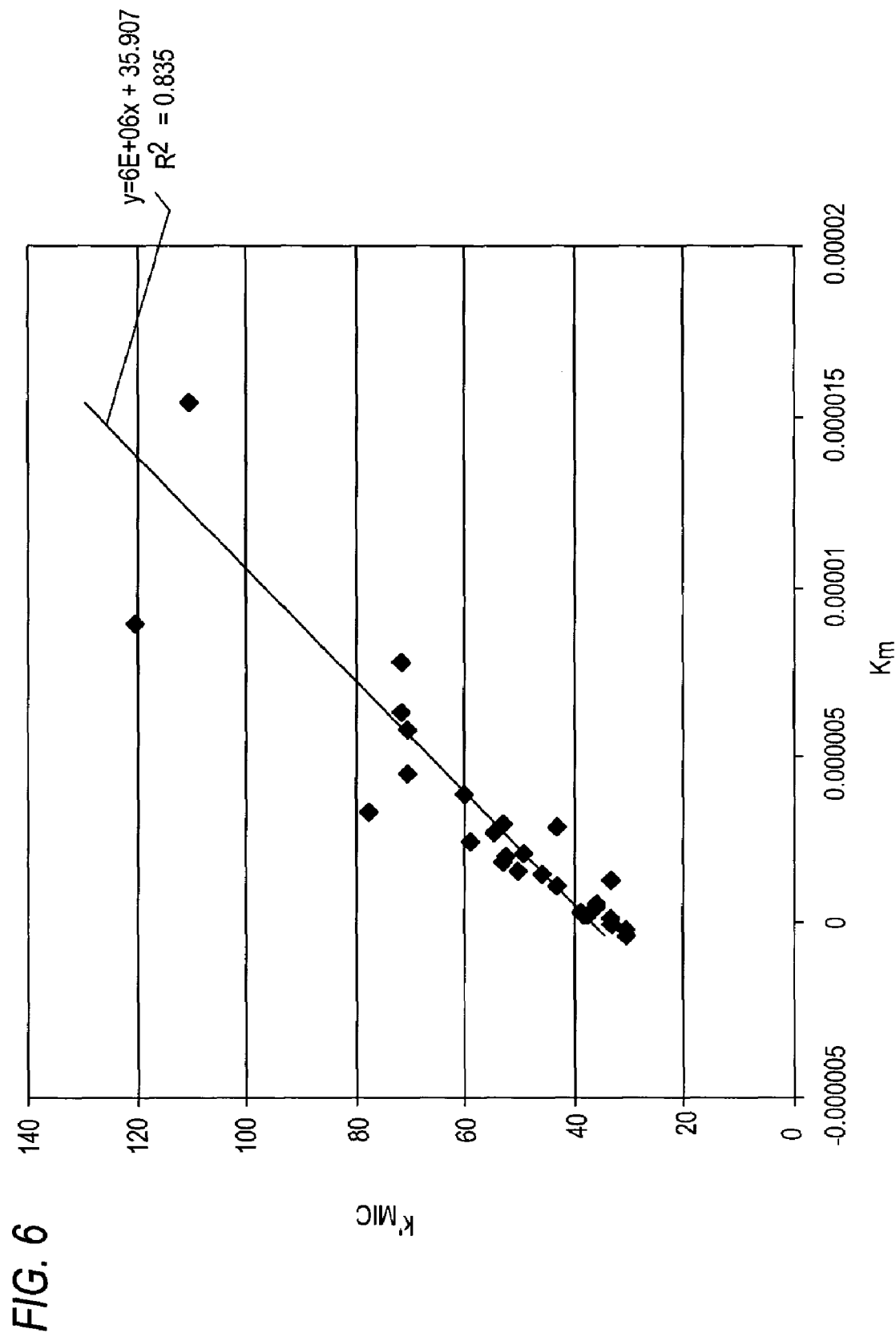
FIG. 6 shows the correlation between the measured partition coefficient determined by MIC and the membrane equilibrium constant derived from equation 2, using $D_m$ and $P_{\it{eff}}$ $_{MIC}$ values listed in Table 4 and L=0.36 µm.

*P$_{eff}$ values were determined by single-pass perfusions (Loc-I-Gut).
**P$_{eff}$ values were determined by linear equation in FIG. 6.
***P$_{eff}$ values were obtained from literature.

FIG. 6 shows the correlation between the measured partition coefficient (k') determined by MIC and the membrane equilibrium constant ($K_m$) derived from equation 2 and shown in Table 4.

Figure 7:
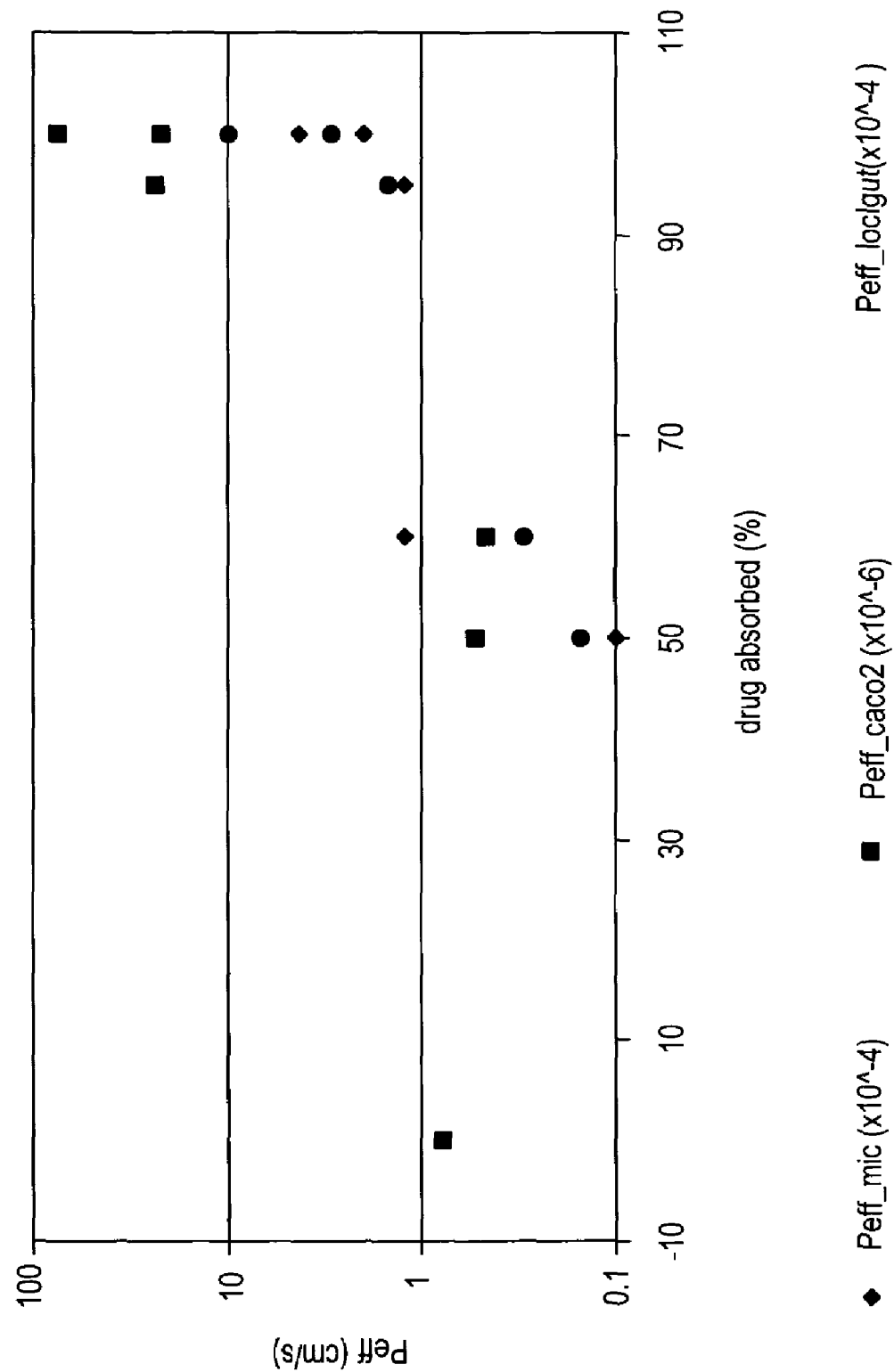
FIG. 7 shows the correlation between in vivo percent drug absorption with the $P_{\it{eff}}$ found by the MIC, Caco-2, and Loc-I-Gut methods. See Example 5.

The comparison of $P_{eff}$ values as determined by MIC, Loc-I-Gut, and Caco-2 methods to in vivo percent absorption is illustrated in Table 6 and FIG. 7. The data corresponds to atenolol, carbamazepine, metoprolol, naproxen, PEG 4000, and propranolol compounds. Additionally, capacity factors for $k'_{MIC}$ and $k'_{IAM}$ were also compared to in vivo percent absorption in FIG. 8.

Example 6 pH Effects on Mucin Immobilized Chromatography Retention Times

One embodiment of this invention is to simulate the healthy and diseased states of a mucosal layer, including that of the GI tract. For example, a diseased state of the mucosal layer can differ in pH and/or thickness. Another embodiment

TABLE 6

In vivo and in vitro absorption values for Loc-I-Gut, MIC, and Caco-2 methods.

| % Absorbed | Drug | $P_{effLoc-I-Gut}$ (×10$^{-4}$ cm/s)* | $P_{effLoc-I-Gut}$ | $K'_{MIC}$ | $P_{effMIC}$ (×10$^{-4}$ cm/s)** | $P_{effCaco-2}$ (×10$^{-6}$ cm/s)*** |
|---|---|---|---|---|---|---|
| 100 | propranolol | 2.9 | 2.2 | 70.43 | 4.24 | 21.8 |
| 100 | Naproxen | 8.0 | 4.2 | 50.43 | 2.01 | 74.2 |
| 95 | metoprolol | 1.5 | 0.9 | 43.29 | 1.21 | 23.7 |
| 60 | terbutaline | 0.3 | 0.3 | 43.29 | 1.21 | 0.47 |
|  | carbamazepine | 4.3 | 2.7 | 59.00 | 2.96 | 19.9 |
| 50 | atenolol | 0.15 | 2.0 | 30.43 | −0.22 | 0.53 |
| 0 | PEG 4000 | 0 | 0 | 33.29 | 0.09 | 0.97 |

*$P_{eff}$ values were determined by single-pass perfusions (Loc-I-Gut).
**$P_{eff}$ values were determined by linear equation in FIG. 6.
***$P_{eff}$ values were obtained from literature.

Figure 8:
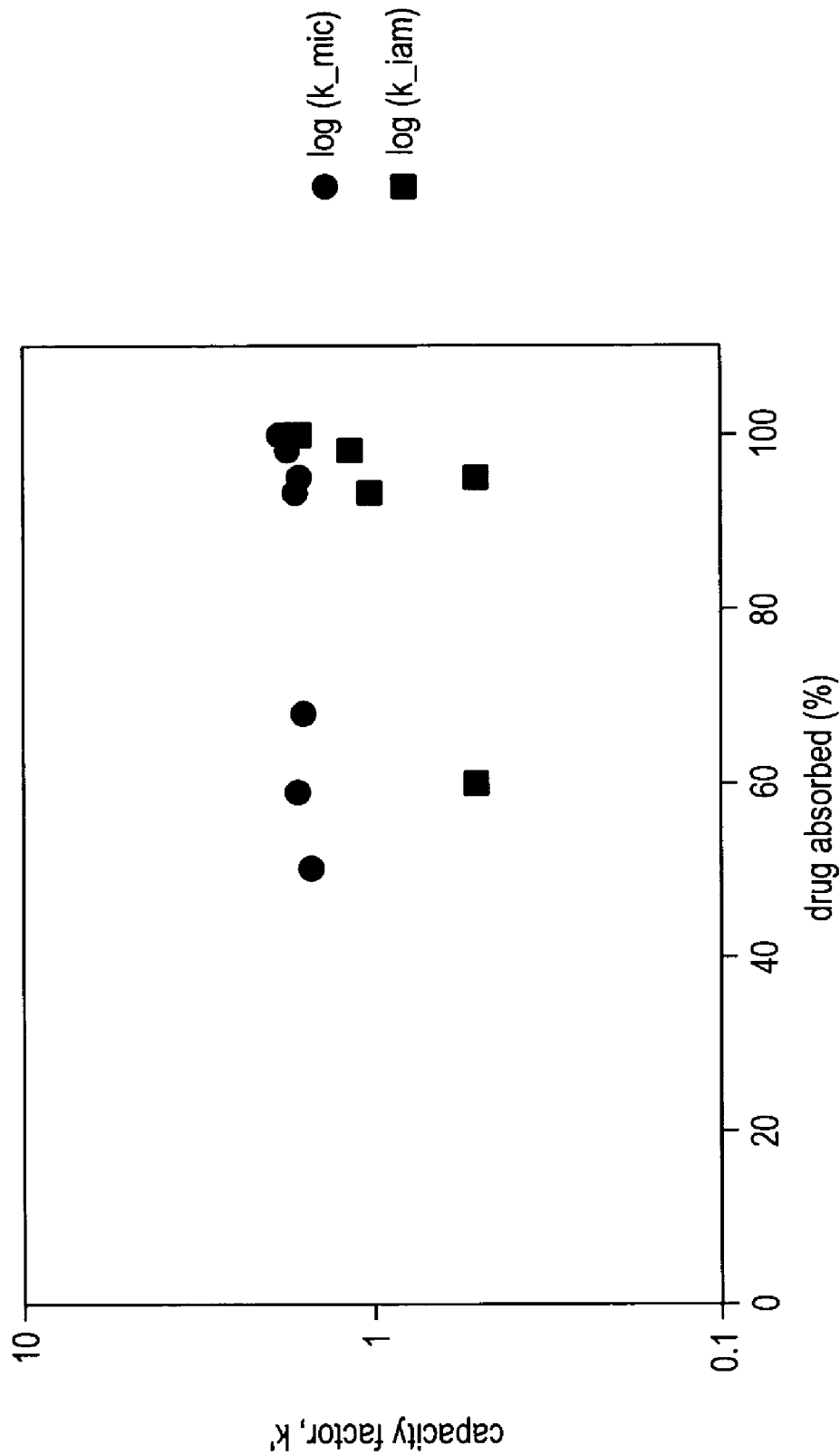
FIG. 8 shows the correlation between in vivo absorption values with $k'_{IAM}$ and $k'_{MIC}$. See Example 5.

The $P_{eff}$ data from the Loc-I-gut, Caco-2 and MIC methods were correlated with in vivo drug absorption. See FIG. 7. In the case of the Caco-2 model, the pattern of correlation was not as clear as that of IAM and MIC. The correlation between in vivo drug absorption with the partition ratios for IAM and MIC is shown in FIG. 8 and Table 7. Similarly, the partition ratios for IAM do not correlate as strongly with in vivo drug absorption as MIC. Thus, MIC appears to be a better in vitro model for drug absorption than either the IAM or Caco-2 models.

TABLE 7

Correlation between capacity factors for pharmaceutical compounds passively absorbed.

| % Absorbed | Drug | log $k'_{MIC}$ | log $k'_{IAM}$ | $\delta^2$ |
|---|---|---|---|---|
| 100 | Antipyrine | 1.89 | −0.02 | 1.91 |
| 100 | corticosterone | 1.78 | 1.60 | 0.18 |
| 100 | Propranolol | 1.85 | 1.75 | 0.10 |
| 98 | Warfarin | 1.74 | 1.15 | 0.59 |
| 95 | Metoprolol | 1.64 | 0.50 | 1.14 |
| 60 | Terbutaline | 1.64 | 0.50 | 1.14 |

[1] Bioavailability is defined by the equation F = fa (1 − $E_G$) (1 − $E_H$) (Lennernäs, H., "Human Perfusion Studies" in Oral Drug Absorption, Prediction and Assessment, Dressman, J. and Lennernäs, H., Eds., 106, 99-117 (2000)).
[2] $\delta$ = log $k'_{MIC}$ − log $k'_{IAM}$.

of this invention is to mimic different parts of the GI tract by changing pH. For these reasons, the influence of pH on drug retention times was measured on columns having two different mucin layer thicknesses, 0.32 μm (column prepared with a 1:2 wt % of mucin to PC IAM particles) and 0.36 μm (column prepared with a 2:1 wt % of mucin to PC IAM particles)(Table 8). Mucin thickness was calculated as described in Example 3. The influence of pH on drug retention time was measured by using different mobile phase buffers adjusted to pH 3, 5 or 7 on either the 0.32 μm or 0.36 μm column. The data in Table 8 demonstrates that, with few exceptions, the drug retention times, calculated as partition ratios (k), at pH 3, 5 or 7 were longer on the 0.32 μm column (1:2 wt % ratio of mucin to PC IAM particles) than on the 0.36 μm column (2:1 wt % ratio of mucin to PC IAM particles). This demonstrates that different thicknesses of mucin influence the partition ratio and thus can be used to mimic different mucosal linings or diseased states.

In addition, most of the drugs exhibited different retention times for runs performed at pH 3, 5 or 7 on a single column. Because mucin is comprised of hydrophilic groups that are capable of being ionized in acidic or basic environments, the corresponding interaction between the hydrophilic groups of mucin and those of the drug compound would also be modulated by change in pH environment. See Table 8. These data demonstrate that MIC can be used to mimic mucosal linings of different pH and thickness.

TABLE 8 pH Dependence of Partition Ratio for Drug Candidates on MIC.

| Compound | (1:2) k' (pH 7) | (1:2) k' (pH 5) | (1:2) k' (pH 3) | (2:1) k' (pH 7) | (2:1) k' (pH 5) | (2:1) k' (pH 3) |
|---|---|---|---|---|---|---|
| antipyrine | 50.67 | 54.00 | 54.00 | 40.67 | 39.00 | 40.43 |
| glybenclamide | 30.67 | 30.67 | none | 34.00 | 19.00 | none |
| verapamil | 55.67 | 30.67 | 27.33 | 45.67 | 24.71 | 34.71 |
| nifedipine | 19.00 | 22.33 | 17.33 | 17.33 | 14.71 | 14.71 |
| glipzide | 19.00 | 30.67 | 32.33 | 19.00 | 23.29 | 24.71 |
| metoclorpramide | 107.33 | 65.67 | 57.33 | 94.00 | 53.29 | 47.57 |
| di-propranol | 99.00 | 92.33 | 75.67 | 99.00 | 59.00 | 49.00 |
| hydrochlorothiazide | 67.33 | 70.67 | 70.67 | 55.67 | 13.29 | 14.71 |
| Phenoxybenzamine HCl | 29.00 | 29.00 | 20.67 | 15.67 | 17.57 | 20.43 |
| ranitidine•HCl | 32.33 | 35.67 | 35.67 | 37.33 | 27.57 | 27.57 |
| trimethoprim | 70.67 | 67.33 | 57.33 | 57.33 | 31.86 | 26.14 |
| haloperidol | 110.67 | 44.00 | 30.67 | 95.67 | 34.71 | 23.29 |
| creatine | 39.00 | 39.00 | 39.00 | 32.33 | 23.29 | 20.43 |
| alprenolol | 42.33 | 64.00 | 54.00 | 82.33 | 49.00 | 43.29 |
| acetominophenol | 64.00 | 65.67 | 64.00 | 62.33 | 51.86 | 50.43 |
| caffein | 45.67 | 44.00 | 44.00 | 39.00 | 34.71 | 34.71 |
| leucine | none | none | none | none | none | none |
| enalapril maleate | 34.00 | 37.33 | 27.33 | 20.67 | 21.86 | 31.86 |
| furoseimide | 35.67 | 37.33 | 40.67 | 25.67 | 27.57 | 30.43 |
| atenolol | 39.00 | 39.00 | 39.00 | 37.33 | 31.86 | 29.00 |
| naproxen | 90.67 | 40.67 | 32.33 | 77.33 | 31.86 | 20.43 |
| terbutalin | 39.00 | 49.00 | 45.67 | 35.67 | 37.57 | 34.71 |
| ketoproten | 82.33 | 29.00 | 25.67 | 70.67 | 27.57 | 20.43 |
| 3,4-dihydrophenylalanine | 25.67 | 25.67 | 25.67 | 22.33 | 20.43 | 19.00 |
| metoprolol | 47.33 | 50.67 | 50.67 | 35.67 | 41.86 | 36.14 |
| corticosterone | 24.00 | 22.33 | 24.00 | 24.00 | 20.43 | 20.43 |
| timolol | 32.33 | 30.67 | 44.00 | 35.67 | 27.57 | 33.29 |
| sulfasalazine | 24.00 | 85.67 | 87.33 | 22.33 | 67.57 | 70.43 |
| labetalol | 32.33 | 24.00 | 24.00 | 132.33 | 90.43 | 79.00 |
| warfarin | 39.00 | 30.67 | 25.67 | 19.00 | 24.71 | 21.86 |
| acycloguanosine | 25.67 | 15.67 | 25.67 | 24.00 | 20.43 | 20.43 |
| cimetidine | 44.00 | 29.00 | 25.67 | 35.67 | 23.29 | 17.57 |
| glycine | none | none | none | none | none | none |
| quinidine | 99.00 | 87.33 | 49.00 | 132.33 | 63.29 | 37.57 |
| amethopterin | 12.33 | 29.00 | 10.67 | 57.33 | 13.29 | none |
| acetylsalicyclic acid | 22.33 | 40.67 | 34.00 | 20.67 | 24.71 | 30.43 |

Example 7

Figure 9:
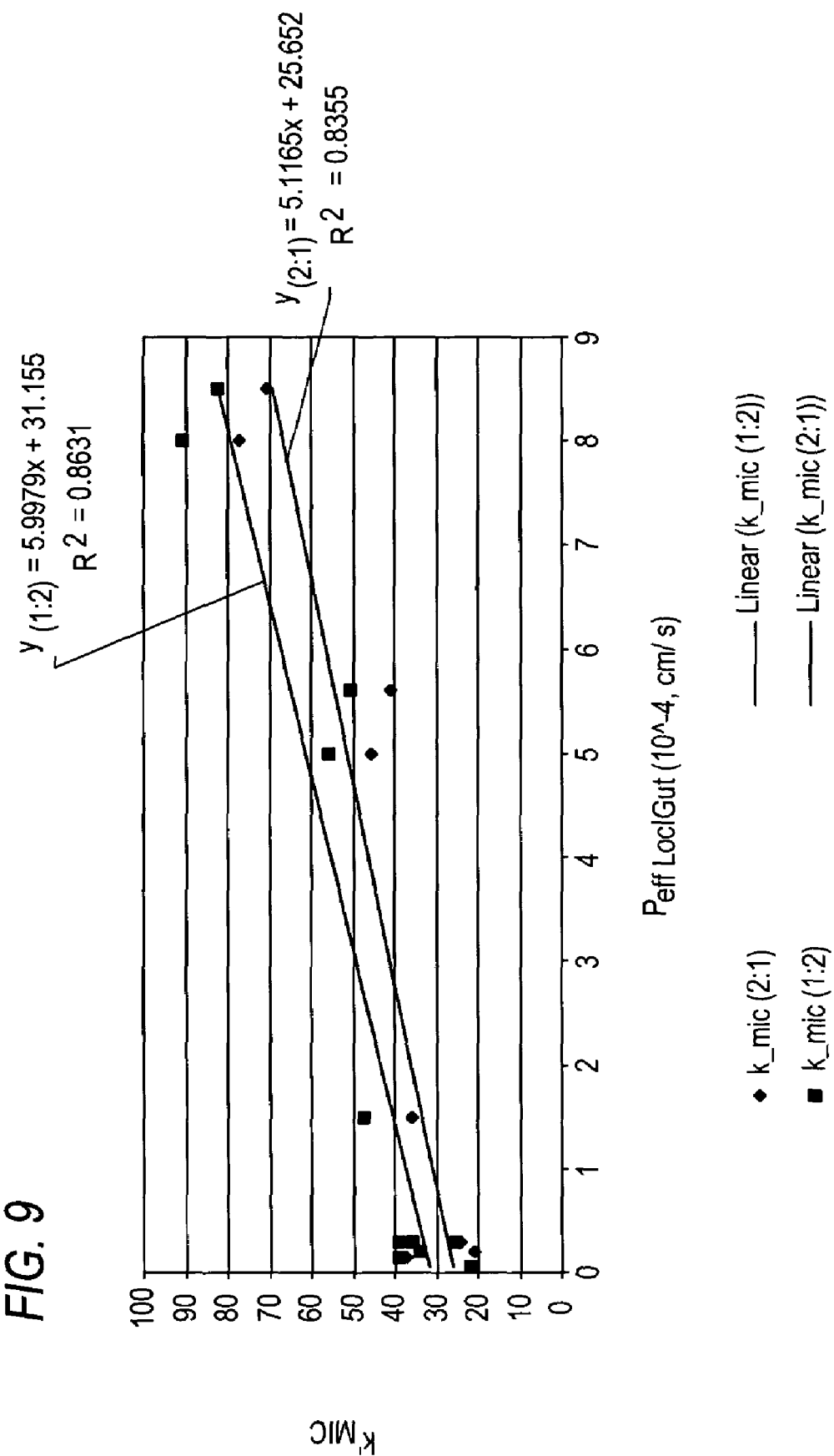
FIG. 9 shows the correlation between $P_{\it{eff\,Loc\text{-}I\text{-}Gut}}$ and $k'_{MIC\,(2:1)}$ and $k'_{MIC\,(1:2)}$. See Example 7.

Correlation Between Effective Permeability and Capacity Factors for Different Mucin Layer Thickness FIG. 9 and Table 9 show the correlation between effective permeability, $P_{effLoc-I-Gut}$, and capacity factors $k'_{MIC(2:1)}$ and $k'_{MIC(1:2)}$ measured at pH 7 (see Table 8). Capacity factors were calculated from drug retention times collected on columns having two different mucin layer thicknesses, 0.32 µm (column prepared with a 1:2 wt % of mucin to PC IAM particles) and 0.36 µm (column prepared with a 2:1 wt % of mucin to PC IAM particles). See Example 6. A linear fit was used to correlate mean data of $P_{effLoc-I-Gut}$ and $k'_{MIC(2:1)}$ and $k'_{MIC(1:2)}$ ($R^2=0.836$ and $R^2=0.863$, respectively). These data indicate a good correlation between drug permeability coefficients derived from in vivo absorption experiments and drug partition coefficients calculated from in vitro experiments according to this invention. MIC thus serves as a valid model for estimating in vitro drug permeability coefficients.

TABLE 9

Effective permeability and capacity factors $k'_{MIC(2:1)}$ and $k'_{MIC(1:2)}$.

| Drug | $P_{effLoc-I-Gut}$ (×10$^{-4}$ cm/s) * | $k'_{MIC}$ (2:1) | $k'_{MIC}$ (1:2) |
|---|---|---|---|
| antipyrine | 5.6 | 40.7 | 50.7 |
| atenolol | 0.2 | 37 | 39 |
| furosemide | 0.3 | 25.7 | 35.7 |
| ketoprofen | 8.5 | 70.7 | 82.3 |
| metoprolol | 1.5 | 35.7 | 47.3 |
| naproxen | 8.0 | 77.3 | 90.7 |
| terbutaline | 0.3 | 35.7 | 39 |
| verapamil | 5.0 | 45.7 | 55.7 |
| enalapril maleate | 0.2 | 20.7 | 34 |
| propranolol | 2.9 | | |
| creatine | 0.3 | 24 | 25.7 |
| PEG 4000 | 0 | 22 | 22 |

*$P_{eff}$ values were determined by single-pass perfusions (Loc-I-Gut).

We claim:

1. A composition comprising:
   (a) a mucin-type protein wherein said mucin-type protein is selected from the group consisting of MUC1, MUC2, MUC3, MUC4, MUC5AC, MUC5B, MUC6, MUC7, MUC8, MUC9, MUC11 and MUC12;
   (b) an amphiphilic molecule, wherein said amphiphilic molecule is selected from the group consisting of phospholipids, phosphoglycerides, sphingolipids, prostaglandins, saturated fatty acids, unsaturated fatty acids, soaps, phosphatidyl choline, phosphatidylethanolamine, phosphatidylglycerol, phosphatidic acid, and phosphatidylserine;
   (c) a solid support matrix; and
   (d) a drug;
   wherein said mucin-type protein is non-covalently immobilized to said solid support matrix; said solid support matrix is surface modified with the amphiphilic molecule;
   and said drug interacts with said mucin-type protein.

2. The composition according to claim 1, wherein there is more than one type of mucin-type protein immobilized to the solid support matrix.

3. The composition according to claim 1, further comprising one or more components of a mucus layer selected from the group consisting of lipids, non-mucin proteins, deoxyribonucleic acid (DNA), ribonucleic acid (RNA) and carbohydrates.

4. The composition according to claim 1, wherein said mucin-type protein is a secreted mucin, a membrane-bound mucin, or a combination thereof.

5. The composition according to claim 1, wherein said mucin-type protein contains threonine and serine amino acid residues that are fully O-linked glycosylated, partially O-linked glycosylated, or non-glycosylated at the hydroxyl group of the amino acid side chain.

6. The composition according to claim 5, wherein said side chain is O-linked glycosylated with a carbohydrate selected from the group consisting of monosaccharides, disaccharides, oligosaccharides, and polysaccharides.

7. The composition according to claim 6, wherein said oligosaccharide is selected from the group consisting of galactosyl β(1-3)-N-acetylgalactosamine α(1-O—) [Gal β(1-3)-GalNAc α(1-O)—], galactosyl β(1-3)-N-acetylglucosaminyl-β(1-6)-N-acetylglactosamine α(1-O)-[Gal β(1-3)-[GlcNAc β(1-6)]-GalNAc α(1-O)—], N-acetylglucosaminyl-β(1-3)-N-acetylgalactoamine α(1-O)-[GlcNAc β(1-3)-GalNAc α(1-O)-], N-acetylglucosaminyl-β(1-3)-N-acetylglucosaminyl-β(1-6)-N-acetylgalactosamine α-(1-O)-[GlcNAc β(1-3)-[GlcNAc β(1-6)]-GalNAc α-(1-O)—], N-acetylgalactosaminyl-α(1-3)-N-acetylgalactosamine α-(1-O)-[GalNAc α(1-3)-GalNAc α-(1-O)—], and galactosyl β(1-3)-galactosyl β(1-6)-N-acetylgalactosamine α(1-O)-[Gal β(1-3)-[Gal β(1-6)]GalNAc α(1-O)—].

8. The composition according to claim 7, wherein said oligosaccharide is Gal β(1-3)GaNAc α-.

9. The composition according to claim 6, wherein said monosaccharide is N-acetylgalactosamine (GalNAc).

10. The composition according to claim 1, wherein said mucin-type protein is derived from a mucin from an epithelial cell surface coating selected from the group consisting of gastrointestinal tract, eye, trachea, lung, salivary gland, sweat gland, breast, reproductive tract, pancreatic duct, gall bladder and urethra.

11. The composition according to claim 1, wherein said solid support matrix comprises an inorganic molecule, a polymer or a copolymer.

12. The composition according to claim 11, wherein said solid support matrix is an inorganic molecule selected from the group consisting of a silicate, alumina, hydroxyapatite, zeolite, germanate, phosphate, and a mixture thereof.

13. The composition according to claim 12, wherein said inorganic molecule is a functionalized silicate.

14. The composition according to claim 13, wherein said functionalized silicate is selected from the group consisting of 3-aminopropyl silica, 1-allyl silica, 3-(3,4-cyclohexyldiol) propyl, 3-(diethylenetriamino)propyl, 4-ethyl benzenesulfonamide, 3-mercaptopropyl, propionyl chloride, 3-(2-succinic anhydride)propyl, and 3-(ureido)propyl.

15. The composition according to claim 1, wherein said amphiphilic molecule is a phospholipid.

16. The composition according to claim 1, wherein said amphiphilic molecule is selected from the group consisting of phosphoglycerides, spingolipids, prostaglandins, saturated fatty acids, unsaturated fatty acids and soaps.

17. The composition according to claim 1, wherein said amphiphilic molecule is phosphatidyl choline.

18. The composition according to claim 1 wherein said mucin protein is selected from the group consisting of MUC2, MUC5AC, MUC5B and MUC6.

* * * * *